United States Patent
Kitade et al.

(10) Patent No.: US 9,120,780 B2
(45) Date of Patent: *Sep. 1, 2015

(54) INDOLE OR INDAZOLE DERIVATIVE OR SALT THEREOF

(75) Inventors: Makoto Kitade, Nagareyama (JP); Shuichi Ohkubo, Hanno (JP); Chihoko Yoshimura, Tsukuba (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/978,632

(22) PCT Filed: Jan. 6, 2012

(86) PCT No.: PCT/JP2012/050140
§ 371 (c)(1),
(2), (4) Date: Jul. 8, 2013

(87) PCT Pub. No.: WO2012/093707
PCT Pub. Date: Jul. 12, 2012

(65) Prior Publication Data
US 2013/0289072 A1   Oct. 31, 2013

(30) Foreign Application Priority Data
Jan. 7, 2011   (JP) ................. 2011-002147

(51) Int. Cl.
*C07D 209/04* (2006.01)
*C07D 213/02* (2006.01)
(Continued)

(52) U.S. Cl.
CPC .......... *C07D 401/14* (2013.01); *A61K 31/4178* (2013.01); *A61K 31/4439* (2013.01); *C07D 403/14* (2013.01)

(58) Field of Classification Search
CPC ... C07D 209/04; C07D 213/02; A61K 31/404
USPC ........................ 514/337; 546/275.7
See application file for complete search history.

(56) References Cited

U.S. PATENT DOCUMENTS 8,779,142 B2 *  7/2014  Kitade et al. .................. 546/118
2004/0034061 A1  2/2004  Nakazato et al.
(Continued)

FOREIGN PATENT DOCUMENTS

JP   57-203068 A    12/1982
JP   2004-502685 A   1/2004
(Continued)

OTHER PUBLICATIONS

Gura; Science; 1997: vol. 278. No. 5340, pp. 1041-1042.*
(Continued)

*Primary Examiner* — John Mabry
*Assistant Examiner* — Daniel Carcanague
(74) *Attorney, Agent, or Firm* — Oblon, McClelland, Maier & Neustadt, L.L.P.

(57) ABSTRACT

The invention provides an indazole compound of formula (I) which is capable of inhibiting HSP90 and shows a cytostatic effect on cancer cells:

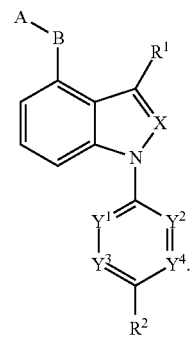

(I)

7 Claims, 2 Drawing Sheets

(51) Int. Cl.
*A61K 31/404* (2006.01)
*A61K 31/4439* (2006.01)
*A61K 31/4178* (2006.01)
*C07D 401/14* (2006.01)
*C07D 403/14* (2006.01)

(56) References Cited

U.S. PATENT DOCUMENTS

| | | | |
|---|---|---|---|
| 2007/0185184 | A1 | 8/2007 | Hanson et al. |
| 2008/0119457 | A1 | 5/2008 | Huang et al. |
| 2008/0176840 | A1* | 7/2008 | Sun et al. .................... 514/230.5 |
| 2011/0028464 | A1 | 2/2011 | Tsantrizos et al. |
| 2011/0039889 | A1 | 2/2011 | Eldred et al. |
| 2011/0166169 | A1 | 7/2011 | Ruxer et al. |
| 2012/0010241 | A1 | 1/2012 | Bertin et al. |
| 2012/0108589 | A1 | 5/2012 | Kitade et al. |

FOREIGN PATENT DOCUMENTS

| | | |
|---|---|---|
| WO | WO 2007/035620 A2 | 3/2007 |
| WO | WO 2008/024978 A2 | 2/2008 |
| WO | WO 2008/026704 A1 | 3/2008 |
| WO | WO 2009/062289 A1 | 5/2009 |
| WO | WO 2009/073777 A1 | 6/2009 |
| WO | WO 2009/122034 A2 | 10/2009 |
| WO | WO 2009/133136 A1 | 11/2009 |
| WO | WO 2010/106290 A1 | 9/2010 |
| WO | WO 2011/004610 A1 | 1/2011 |

OTHER PUBLICATIONS

Dymock; Expert Opinion on Therapeutic Patents 2004, 14(6), 837-847.*
Bagatell; Molecular Cancer Therapy, 2004 1021-1030.*
Whitesell; Heat Shock Proteins in Cancer, 2007, 253-274.*
Trepel; Nat. Rev. Cancer, 10(8); 2010:537-549.*
Johnson; British Journal of Cancer 2001, 84, 1424-1431.*
U.S. Appl. No. 13/978,613, filed Jul. 8, 2013, Kitade, et al.
Gilman, H. et al., "Some Substituted Isoquinolines", Journal of the American Chemical Society, vol. 69, pp. 1946 to 1948, Table 1, (1947).
Whitesell, L. et al., "HSP90 and the Chaperoning of Cancer", Nature Reviews Cancer, vol. 5, pp. 761 to 772, (Oct. 2005).
Kamal, A. et al., "Therapeutic and diagnostic implications of Hsp90 activation", Trends in Molecular Medicine, vol. 10, No. 6, pp. 283 to 290, (Jun. 2004).
Banerji, U., "Heat Shock Protein 90 as a Drug Target: Some Like It Hot", Clin Cancer Res, vol. 15, No. 1, pp. 9 to 14, (Jan. 1, 2009).
Taldone, T. et al., "Targeting Hsp90: small-molecule inhibitors and their clinical development", Current Opinion in Pharmacology, vol. 8, pp. 370 to 374, (2008).
Li, Y. et al., "New developments in Hsp90 inhibitors as anti-cancer therapeutics: Mechanisms, clinical perspective and more potential", Drug Resistance Updates, vol. 12, pp. 17 to 27, (2009).
Luo, W. et al., "Heat shock protein 90: translation from cancer to Alzheimer's disease treatment", BMC Neuroscience, vol. 9 (Suppl. 2): S7, pp. 1 to 8, (2008).
International Search Report Issued Feb. 28, 2012 in PCT/JP2012/50141 Filed Jan. 6, 2012.
Combined Chinese Office Action and Search Report issued Mar. 20, 2014 in Patent Application No. 201280004870.5 (with partial English language translation).
U.S. Appl. No. 14/242,063, filed Apr. 1, 2014, Kitade, et al.

* cited by examiner

INDOLE OR INDAZOLE DERIVATIVE OR SALT THEREOF

This application is a National Stage of PCT?JP12050140 filed Jan. 6, 2012 and claims the benefit of JP 2011-002147 filed Jan. 7, 2011.

FIELD OF THE INVENTION

The present invention relates to a novel indole or indazole derivative or a salt thereof, and a drug containing the same, particularly, an agent for prevention and/or treatment of cancer, etc., based on HSP90 inhibitory activity.

BACKGROUND OF THE INVENTION

A group of proteins called molecular chaperons is a multifunctional protein, which promotes formation of functional structures of other proteins or maintains these structures, promotes correct association, inhibits unnecessary aggregation, protects other proteins from degradation, and promotes secretion (Non-Patent Document 1). HSP90 is a molecular chaperon as abundant as approximately 1 to 2% of all intracellular soluble proteins and is however unnecessary for the biosynthesis of the majority of polypeptides, unlike other chaperon proteins (Non-Patent Document 1). Signaling-related factors (e.g., ERBB1/EGFR, ERBB2/HER2, MET, IGF1R, KDR/VEGFR, FLT3, ZAP70, KIT, CHUK/IKK, BRAF, RAF1, SRC and AKT), cell cycle regulators (e.g., CDK4, CDK6, Cyclin D, PLK1, and BIRC5), and transcriptional regulators (e.g., HIF-1α, p53, androgen receptor, estrogen receptor, and progesterone receptor) are known as main client proteins whose structure formation or stability is regulated by HSP90 through the interaction therebetween (Non-Patent Documents 2 and 3). HSP90 is deeply involved in cell proliferation or survival by maintaining the normal functions of these proteins. Furthermore, HSP90 is required for the normal functions of mutated or chimeric factors (e.g., BCR-ABL and NPM-ALK) which cause carcinogenesis or exacerbation of cancer. This indicates the importance of HSP90 particularly for processes such as carcinogenesis, cancer survival, growth, exacerbation and metastasis (Non-Patent Document 2).

The inhibition of the chaperon functions of HSP90 by specific inhibitors such as geldanamycin causes the inactivation, destabilization and degradation of the client proteins, resulting termination of cell proliferation or induction of apoptosis (Non-Patent Document 4). Considering the physiological functions of HSP90, HSP90 inhibitors are characterized in that they can simultaneously inhibit a plurality of signaling pathways involved in cancer survival/growth. Thus, the HSP90 inhibitors can serve as drugs showing an extensive and effective anticancer activity. Moreover, from the findings that cancer cell-derived HSP90 shows a higher activity and higher affinity for ATP or inhibitors than those of normal cell-derived HSP90, it has been expected that the HSP90 inhibitors would serve as drugs showing high selectivity for cancer (Non-Patent Document 5).

Currently, the clinical development of a plurality of HSP90 inhibitors as anticancer agents is ongoing. The most advancing geldanamycin derivative 17-allylamino-17-desmethoxygeldanamycin (17-AAG) is under development as single agents as well as under test on the combined use with various anticancer agents (Non-Patent Documents 3 and 4). However, the problems of 17-AAG, such as poor solubility, instability in solutions, low oral absorption, and liver toxicity, have also been pointed out (Non-Patent Documents 4 and 5). Thus, a new type of HSP90 inhibitor has been desired. It has also been reported that HSP90 inhibitors not only show an anticancer activity but also can serve as therapeutic agents for autoimmune disease, inflammatory disease, central nervous system disease (e.g., Parkinson's disease, Alzheimer's disease, and Huntington's disease), viral infections, cardiovascular disease, etc. (Non-Patent Documents 2 and 6).

CITATION LIST

Patent Document

Patent Document 1: WO 2007/035620
Patent Document 2: WO 2008/024978

Non-Patent Document

Non-Patent Document 1: Nature Reviews Cancer 5, 761-772 (2005)
Non-Patent Document 2: TRENDS in Molecular Medicine 6, 17-27 (2004)
Non-Patent Document 3: Clin Can Res 15, 9-14 (2009)
Non-Patent Document 4: Current Opinion in Pharmacology 8, 370-374 (2008)
Non-Patent Document 5: Drug Resistance Updates 12, 17-27 (2009)
Non-Patent Document 6: BMC Neuroscience 9 (Suppl. 2), 2008

SUMMARY OF THE INVENTION

Problem to be Solved by the Invention

The purpose of the present invention is to provide a novel indazole compound which is capable of inhibiting HSP90 and shows a cytostatic effect on cancer cells. Another purpose of the present invention is to provide a drug useful for preventing and/or treating, on the basis of an HSP90 inhibitory effect, a disease in which HSP90 participates, in particular, cancer.

Means for Solving the Problem

The present inventors have intensively studied compounds showing an HSP90 inhibitory activity and consequently completed the present invention by finding that a novel compound represented by the general formula (I) shown below, which has two unsaturated heterocyclic groups at the $4^{th}$ position of the indole ring/indazole ring in the general formula (I), exhibits a remarkably excellent inhibitory activity against HSP90 and further exhibits an excellent cytostatic effect on cancer cells, and thus is useful for prevention or treatment of a disease in which HSP90 participates, in particular, as an anticancer agent.

Specifically, the present invention provides a compound represented by the following general formula (I), or a salt thereof:

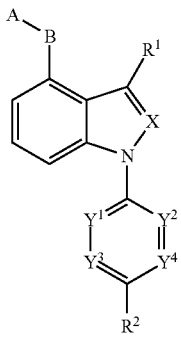

(I)

(wherein;

X represents CH or N;

any one or two of $Y^1$, $Y^2$, $Y^3$, and $Y^4$ represent C—$R^3$ or N, and the others represent CH;

A and B are the same or different and represent an optionally substituted monocyclic unsaturated heterocyclic group having 1 to 4 heteroatoms selected from N, S, and O;

$R^1$ represents a hydrogen atom, an optionally substituted alkyl group having 1 to 6 carbon atoms, an optionally substituted cycloalkyl group having 3 to 7 carbon atoms, or an optionally substituted alkenyl group having 2 to 6 carbon atoms;

$R^2$ represents a hydrogen atom, a halogen atom, a cyano group, or —CO—$R^4$;

$R^3$ represents a hydrogen atom, a halogen atom, an alkyl group having 1 to 6 carbon atoms, an alkoxy group having 1 to 6 carbon atoms, —CO—$R^5$, —N($R^6$)($R^7$), or —S—$R^8$:

$R^4$ and $R^5$ are the same or different and represent a hydroxyl group, an amino group, or an alkylamino group having 1 to 6 carbon atoms;

$R^6$ and $R^7$ are the same or different and represent a hydrogen atom, an alkyl group having 1 to 6 carbon atoms, a cycloalkyl group having 3 to 7 carbon atoms and optionally having a hydroxyl group, an aromatic hydrocarbon group, a saturated heterocyclic group, or an unsaturated heterocyclic group, or $R^6$ and $R^7$ when taken together with the nitrogen atom to which they are bonded optionally form a saturated heterocyclic group; and $R^8$ represents an optionally substituted cycloalkyl group having 3 to 7 carbon atoms or an optionally substituted aromatic hydrocarbon group).

The present invention also provides a drug containing the compound represented by the general formula (I), or the salt thereof.

Further, the present invention provides a pharmaceutical composition comprising the compound represented by the general formula (I) or the salt thereof and a pharmaceutically acceptable carrier.

Moreover, the present invention provides the compound represented by the general formula (I) or the salt thereof for preventing or treating a disease in which HSP90 participates, in particular, cancer.

Additionally, the present invention provides use of the compound represented by the general formula (I) or the salt thereof for manufacturing a preventive or therapeutic agent for a disease in which HSP90 participates, in particular, cancer.

Furthermore, the present invention provides a method for preventing or treating a disease in which HSP90 participates, in particular, cancer, which method is characterized by administering an effective amount of the compound represented by the general formula (I) or the salt thereof.

Effects of the Invention

The present invention provides a novel compound represented by the general formula (I) or a salt thereof, which is useful as an HSP90 inhibitor.

The compound of the present invention or the salt thereof has been shown to exhibit an excellent HSP90 inhibitory activity and exhibit a cytostatic effect against cancer cells. In addition, the compound of the present invention or the salt thereof is highly safe because the hERG channel inhibitory action which is an index of adverse side effects such as cardiac toxicity is weak. Thus, the compound of the present invention or the salt thereof is useful as a preventive and/or therapeutic agent for a disease involving HSP90, for example, cancer, on the basis of its excellent HSP90 inhibitory activity.

DETAILED DESCRIPTION OF THE INVENTION

Figure 1:
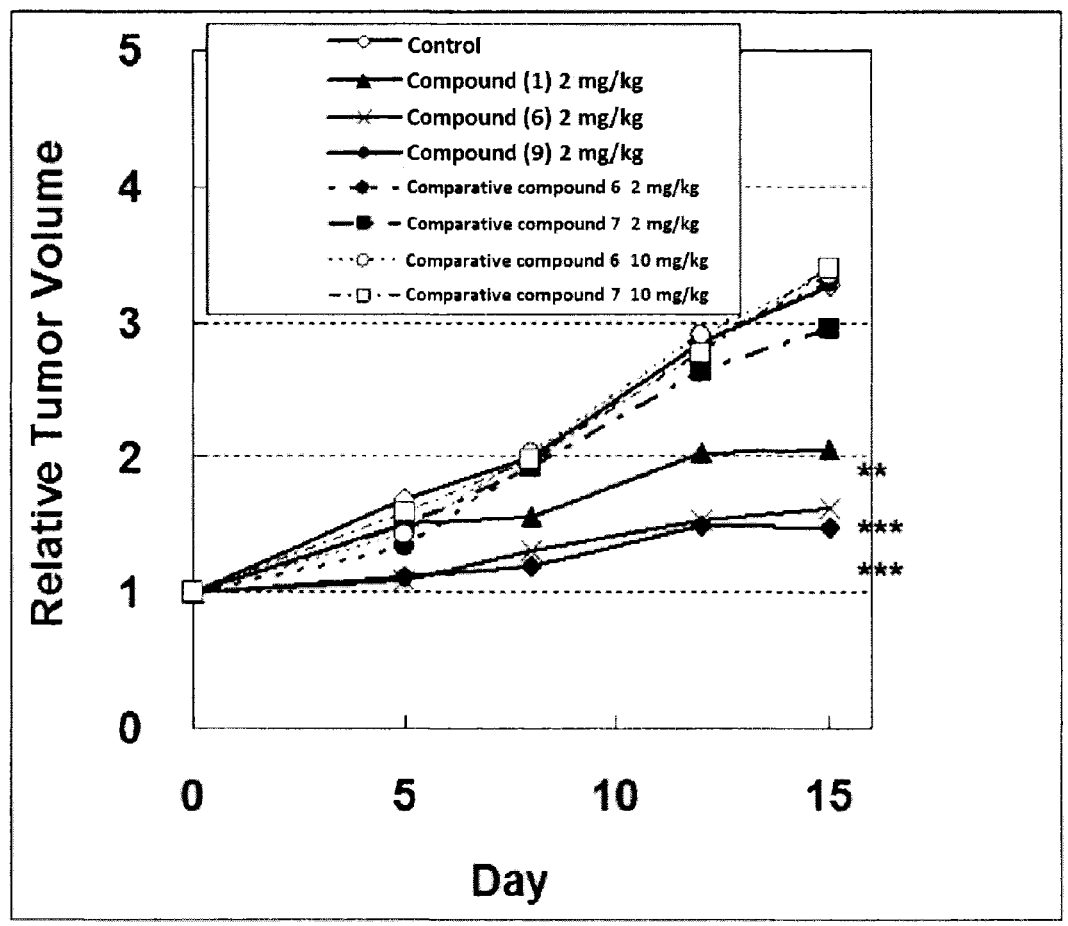
FIG. 1 is a graph showing in vivo anti-tumor effect of the compounds of the present invention.

The compound of the present invention represented by the general formula (I) is an indole or indazole compound characterized by having two unsaturated heterocyclic groups at the $4^{th}$ position of the indole ring/indazole ring represented by A and B in the general formula (I), and is a novel compound which is not described in any of the prior art Documents.

In the present specification, examples of the "substituent" include a halogen atom, a hydroxyl group, a cyano group, an amino group, a nitro group, an oxo group, a carboxyl group, a carbamoyl group, an alkyl group, a cycloalkyl group, an alkenyl group, an alkynyl group, an alkoxy group, an acyl group, an acyloxy group, an alkoxycarbonyl group, a saturated heterocyclic group, an unsaturated heterocyclic group, an aromatic hydrocarbon group, a halogenoalkyl group, an aralkyl group, an alkylamino group, an acylamino group, and an aralkyloxy group. The number of the substituents, if any, is typically 1 to 3.

Examples of the halogen atom included in the substituents include chlorine, bromine, fluorine, and iodine atoms.

The alkyl group included in the substituents preferably refers to a linear or branched alkyl group having 1 to 6 carbon atoms, such as methyl, ethyl, n-propyl, isopropyl, n-butyl, isobutyl, sec-butyl, tert-butyl, pentyl, and hexyl groups.

The cycloalkyl group included in the substituents is preferably a cycloalkyl group having 3 to 7 carbon atoms, and examples thereof include cyclopropyl, cyclobutyl, cyclopentyl, cyclohexyl, and cycloheptyl groups.

The alkenyl group included in the substituents is preferably an alkenyl group having 2 to 6 carbon atoms which contains a carbon-carbon double bond, and examples thereof include vinyl, allyl, methylvinyl, propenyl, butenyl, pentenyl, and hexenyl groups.

The alkynyl group included in the substituents is preferably an alkynyl group having 2 to 6 carbon atoms, which contains a carbon-carbon triple bond, and examples thereof include ethynyl and propargyl groups.

The alkoxy group included in the substituents preferably refers to a linear or branched alkoxy group having 1 to 6 carbon atoms, and examples thereof include methoxy, ethoxy, n-propoxy, isopropoxy, n-butoxy, isobutoxy, and tert-butoxy groups.

The acyl group included in the substituents preferably refers to an alkanoyl group having 1 to 6 carbon atoms or an aroyl group having 7 to 12 carbon atoms, and examples thereof include formyl, acetyl, propionyl, n-butyryl, isobutyryl, valeryl, isovaleryl, pivaloyl, and benzoyl groups.

The acyloxy group included in the substituents refers to an oxy group which is substituted by the acyl group exemplified above, preferably an oxy group which is substituted by an alkanoyl group having 1 to 6 carbon atoms or by an aroyl group having 7 to 12 carbon atoms. Examples thereof include formyloxy, acetoxy, propionyloxy, n-butyryloxy, isobutyryloxy, valeryloxy, isovaleryloxy, pivaloyloxy, and benzoyloxy groups.

The alkoxycarbonyl group included in the substituents refers to a carbonyl group which is substituted by the alkoxy group exemplified above, preferably a carbonyl group which is substituted by an alkoxy group having 1 to 6 carbon atoms. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, and tert-butoxycarbonyl groups.

The saturated heterocyclic group included in the substituents preferably refers to a monocyclic or bicyclic 5- to 10-membered saturated heterocyclic group having 1 to 4 of any heteroatom of N, S and O. Examples thereof include pyrrolidinyl, piperidinyl, piperazinyl, hexamethyleneimino, morpholino, thiomorpholino, homopiperazinyl, tetrahydrofuranyl, tetrahydropyranyl, methylenedioxyphenyl, ethylenedioxyphenyl, and dihydrobenzofuranyl groups.

The unsaturated heterocyclic group included in the substituents preferably refers to a monocyclic or bicyclic 5- to 10-membered unsaturated heterocyclic group having 1 to 4 of any heteroatom of N, S and O. Examples thereof include imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzoimidazolyl, benzoxazolyl, benzothiazolyl, purinyl, quinolyl, isoquinolyl, quinazolinyl, and quinoxalyl groups.

The aromatic hydrocarbon group included in the substituents preferably refers to an aromatic hydrocarbon group having 6 to 14 carbon atoms, and examples thereof include a phenyl group and a naphthyl group.

The halogenoalkyl group included in the substituents refers to a group in which one to all hydrogen atom(s) of the alkyl group is/are substituted by the halogen atom(s), preferably a group in which one to all hydrogen atom(s) of the linear or branched alkyl group having 1 to 6 carbon atoms is/are substituted by the halogen atom(s), such as difluoromethyl group and trifluoromethyl group.

The aralkyl group included in the substituents preferably refers to a linear or branched alkyl group having 1 to 6 carbon atoms, which is substituted by an aromatic hydrocarbon group having 6 to 14 carbon atoms. Examples thereof include benzyl, phenylethyl, phenylpropyl, naphthylmethyl, and naphthylethyl groups.

The saturated heterocyclic alkyl group included in the substituents refers to the alkyl group which is substituted by the saturated heterocyclic group exemplified above and preferably refers to the linear or branched alkyl group which is substituted by the monocyclic 5- to 7-membered unsaturated heterocyclic group exemplified above having one or two hetero atoms of any of N, S, and O. Examples thereof include morpholinomethyl and piperidinylethyl groups.

The alkylamino group included in the substituents refers to an amino group which is monosubstituted or disubstituted by the alkyl group exemplified above, preferably an amino group which is monosubstituted or disubstituted by the linear or branched alkyl group having 1 to 6 carbon atoms. Examples thereof include methylamino, ethylamino, diethylamino, methylethylamino, cyclobutylmethylamino, dimethylaminomethyl, and 2-hydroxyethyl(methyl)aminomethyl groups.

The acylamino group included in the substituents refers to an amino group which is substituted by the acyl group exemplified above, preferably an amino group which is substituted by an alkanoyl group having 1 to 6 carbon atoms or by an aroyl group having 7 to 12 carbon atoms. Examples thereof include formylamino, acetylamino, propionylamino, butyrylamino, 2-methylpropionylamino, pivaloylamino, pentanoylamino, 3-methylbutyrylamino, and hexanoylamino groups.

The aralkyloxy group included in the substituents refers to an oxy group which has the aralkyl group exemplified above, and preferably refers to an oxy group which is substituted by a linear or branched alkyl group having 1 to 6 carbon atoms to which an aromatic hydrocarbon group having 6 to 14 carbon atoms is attached. Examples thereof include benzyloxy, phenethyloxy, phenylpropyloxy, naphthylmethyloxy, and naphthylethyloxy groups.

In the general formula (I), X is CH or N, and X is preferably N.

In the general formula (I), the "monocyclic unsaturated heterocyclic group having 1 to 4 heteroatoms selected from N, S and O" in the "optionally substituted monocyclic unsaturated heterocyclic group having 1 to 4 heteroatoms selected from N, S and O", represented by A and B, is preferably a monocyclic 5- to 6-membered unsaturated heterocyclic group having 1 to 3 heteroatoms selected from N, S, and O. Examples of the unsaturated heterocyclic group include imidazolyl, pyrazolyl, thienyl, furyl, pyrrolyl, oxazolyl, oxadiazolyl, isoxazolyl, thiazolyl, isothiazolyl, pyrazolyl, triazolyl, tetrazolyl, pyridyl, pyrazyl, pyrimidinyl, pyridazinyl, and triazyl groups.

The unsaturated heterocyclic group represented by A is preferably a nitrogen-containing 5- to 6-membered ring, such as imidazolyl, pyrazolyl, pyrrolyl, triazolyl, tetrazolyl, pyridyl, pyrazyl, pyrimidinyl, pyridazinyl, and triazyl groups, and is especially preferably pyrazolyl and pyridyl groups.

The unsaturated heterocyclic group represented by B is preferably a nitrogen-containing 5- to 6-membered ring, such as imidazolyl, pyrazolyl, pyrrolyl, triazolyl, tetrazolyl, pyridyl, pyrazyl, pyrimidinyl, pyridazinyl, and triazyl groups, more preferably a nitrogen-containing 5-membered ring, such as imidazolyl, pyrazolyl, pyrrolyl, triazolyl, and tetrazolyl groups, and especially preferably an imidazolyl group.

Examples of the "substituent(s)" in the unsaturated heterocyclic group represented by A and B in the general formula (I) include the substituents exemplified above and the number of the substituent(s) is 1 to 3. The substituent includes preferably a halogen atom, a hydroxyl group, an amino group, a carbamoyl group, an alkyl group having 1 to 6 carbon atoms, a halogenoalkyl group having 1 to 6 carbon atoms, an alkoxy group having 1 to 6 carbon atoms, an alkylamino group having 1 to 6 carbon atoms, an acyl group having 1 to 6 carbon atoms, and an acylamino group having 1 to 6 carbon atoms, and more preferably a halogen atom, a hydroxyl group, an amino group, a carbamoyl group, an alkyl group having 1 to 6 carbon atoms, a halogenoalkyl group having 1 to 6 carbon atoms, and an alkoxy group having 1 to 6 carbon atoms, and especially preferably an alkyl group having 1 to 6 carbon atoms.

Examples of the halogen atom which may be substituted on the unsaturated heterocyclic ring represented by A and B include the halogen atom described above.

Examples of the alkyl group having 1 to 6 carbon atoms which may be substituted on the unsaturated heterocyclic ring represented by A and B include the alkyl group having 1 to 6 carbon atoms exemplified above, and more specific examples thereof include preferably methyl, ethyl, n-propyl, and isopropyl groups, and especially preferably a methyl group.

Examples of the alkoxy group having 1 to 6 carbon atoms which may be substituted on the unsaturated heterocyclic ring represented by A and B include the alkoxy group having 1 to 6 carbon atoms exemplified above, and more specific examples thereof include preferably a methoxy group and an ethoxy group.

Examples of the alkylamino group having 1 to 6 carbon atoms which may be substituted on the unsaturated heterocyclic ring represented by A and B include the alkylamino group having 1 to 6 carbon atoms exemplified above, and more specific examples thereof include preferably methylamino, ethylamino, n-propylamino, and cyclobutylmethylamino groups.

Examples of the acyl group having 1 to 6 carbon atoms which may be substituted on the unsaturated heterocyclic ring represented by A and B include the acyl group having 1 to 6 carbon atoms exemplified above, and more specific examples thereof include preferably formyl, acetyl, and propionyl groups.

Examples of the acylamino group having 1 to 6 carbon atoms which may be substituted on the unsaturated heterocyclic ring represented by A and B include the acylamino group having 1 to 6 carbon atoms exemplified above, and more specific examples thereof include preferably acetylamino and propionylamino groups.

A is preferably an optionally substituted monocyclic 5- to 6-membered unsaturated heterocyclic group having 1 to 3 hetero atoms selected from N, S, and O;

A is further preferably a monocyclic 5- to 6-membered unsaturated heterocyclic group having 1 to 3 hetero atoms selected from N, S, and O and optionally having a substituent selected from a halogen atom, a hydroxyl group, an amino group, a carbamoyl group, an alkyl group having 1 to 6 carbon atoms, a halogenoalkyl group having 1 to 6 carbon atoms, an alkoxy group having 1 to 6 carbon atoms, an alkylamino group having 1 to 6 carbon atoms, an acyl group having 1 to 6 carbon atoms, and an acylamino group having 1 to 6 carbon atoms;

A is further preferably a monocyclic 5- to 6-membered unsaturated heterocyclic group having 1 to 3 hetero atoms selected from N, S, and O, and optionally having an alkyl group having 1 to 6 carbon atoms;

A is further preferably a monocyclic 5- to 6-membered unsaturated heterocyclic group having 1 to 3 nitrogen atoms, and optionally having an alkyl group having 1 to 6 carbon atoms;

A is further preferably an imidazolyl, pyrazolyl, pyrrolyl, triazolyl, pyrazyl, or pyrimidinyl group, which may be substituted by an alkyl group having 1 to 6 carbon atoms; and A is further preferably a pyrazolyl group or a pyridyl group, which may be substituted by an alkyl group having 1 to 6 carbon atoms.

Specific preferable examples of A include a 1-methyl-1H-pyrazol-4-yl group and a pyiridin-3-yl group.

B is preferably an optionally substituted monocyclic 5- to 6-membered unsaturated heterocyclic group having 1 to 3 hetero atoms selected from N, S, and O;

B is further preferably a monocyclic 5- to 6-membered unsaturated heterocyclic group having 1 to 3 hetero atoms selected from N, S, and O, and optionally having a substituent selected from a halogen atom, a hydroxyl group, an amino group, a carbamoyl group, an alkyl group having 1 to 6 carbon atoms, a halogenoalkyl group having 1 to 6 carbon atoms, an alkoxy group having 1 to 6 carbon atoms, an alkylamino group having 1 to 6 carbon atoms, an acyl group having 1 to 6 carbon atoms, and an acylamino group having 1 to 6 carbon atoms;

B is further preferably a monocyclic 5- to 6-membered unsaturated heterocyclic group having 1 to 3 hetero atoms selected from N, S, and O;

B is further preferably a monocyclic 5- to 6-membered unsaturated heterocyclic group having 1 to 3 nitrogen atoms;

B is further preferably a monocyclic 5-membered unsaturated heterocyclic group having 1 to 3 nitrogen atoms;

B is further preferably an imidazolyl, pyrazolyl, pyrrolyl, or triazolyl group; and B is further preferably an imidazolyl group.

Specific preferable examples of B include a 1H-imidazol-1-yl group.

In the general formula (I), the "optionally substituted alkyl group having 1 to 6 carbon atoms" represented by R1 refers to the alkyl group having 1 to 6 carbon atoms and optionally having the substituent described above, and preferably refers to an alkyl group having 1 to 6 carbon atoms and optionally having a halogen atom. Specific examples thereof include preferably methyl, ethyl, n-propyl, isopropyl, n-butyl, isobutyl, sec-butyl, tert-butyl, pentyl, hexyl, difluoromethyl, and trifluoromethyl groups.

In the general formula (I), the "optionally substituted cycloalkyl group having 3 to 7 carbon atoms" represented by R1 refers to the cycloalkyl group having 3 to 7 carbon atoms and optionally having the substituent described above, and preferably refers to an unsubstituted cycloalkyl group having 3 to 7 carbon atoms. Specific examples thereof include preferably cyclopropyl, cyclobutyl, cyclopentyl, and cyclohexyl groups, and more preferably a cyclopropyl group.

The "optionally substituted alkenyl group having 2 to 6 carbon atoms" represented by R1 refers to the alkenyl group having 2 to 6 carbon atoms and optionally having the substituent described above, and preferably refers to an unsubstituted alkenyl group having 2 to 6 carbon atoms. Specific examples thereof include preferably vinyl, allyl, and propenyl groups, and more preferably a vinyl group.

R1 is preferably a hydrogen atom; an alkyl group having 1 to 6 carbon atoms which may have a halogen atom; or a cycloalkyl group having 3 to 7 carbon atoms, and is especially preferably a hydrogen atom or an alkyl group having 1 to 6 carbon atoms and optionally having a halogen atom.

Any one or two of $Y^1, Y^2, Y^3,$ and $Y^4$ represent $C-R^3$ or N, and the others represent CH. Of these, preferably, any one of $Y^1, Y^2, Y^3,$ and $Y^4$ represents $C-R^3$ or N, and the others represent CH. More preferably, among $Y^1, Y^2, Y^3,$ and $Y^4$, any one of them is $C-R^3$, and the others are CH. These preferred aspects are represented by the following structural formulae:

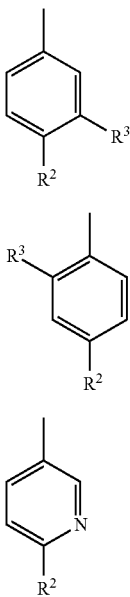

(a1)

(a2)

(a3)

In the above formulae, $R^3$ and $R^4$ have the same meanings as defined above.

Of them, the structures of (a1) and (a2) are more preferable and the structure of (a1) is particularly preferable.

In the general formula (I), the "halogen atom" represented by $R^2$ refers to the halogen atom exemplified above.

$R^2$ is preferably a hydrogen atom, a cyano group, or —CO—$R^4$, more preferably a cyano group or —CO—$R^4$, and further preferably —CO—$R^4$.

In the general formula (I), the alkylamino group having 1 to 6 carbon atoms represented by $R^4$ includes the alkylamino group having 1 to 6 carbon atoms exemplified above.

$R^4$ is preferably a hydroxyl group or an amino group and especially preferably an amino group.

In the general formula (I), the "halogen atom" represented by $R^3$ refers to the halogen atom exemplified above, and is preferably a chlorine atom.

In the general formula (I), the "alkyl group having 1 to 6 carbon atoms" represented by $R^3$ includes the alkyl group having 1 to 6 carbon atoms exemplified above, and is preferably a methyl group, an ethyl group, an n-propyl group, or an isopropyl group.

In the general formula (I), the "alkoxy group having 1 to 6 carbon atoms" represented by $R^3$ includes the alkoxy group having 1 to 6 carbon atoms exemplified above, and is preferably a methoxy group.

$R^3$ is preferably a hydrogen atom, a halogen atom, an alkyl group having 1 to 6 carbon atoms, an alkoxy group having 1 to 6 carbon atoms, or —N($R^6$)($R^7$), more preferably a halogen atom, an alkyl group having 1 to 6 carbon atoms, or —N($R^6$)($R^7$), and especially preferably an alkyl group having 1 to 6 carbon atoms or —N($R^6$)($R^7$).

In the general formula (I), the "alkylamino group having 1 to 6 carbon atoms" represented by $R^5$ includes the alkylamino group having 1 to 6 carbon atoms exemplified above.

$R^5$ is preferably an amino group or an alkylamino group having 1 to 6 carbon atoms and is especially preferably an amino group.

In the general formula (I), the "alkyl group having 1 to 6 carbon atoms" represented by $R^6$ and $R^7$ includes the alkyl group having 1 to 6 carbon atoms exemplified above, and is specifically preferably a methyl group, an ethyl group, an n-propyl group, an isopropyl group, an n-butyl group, an isobutyl group, a sec-butyl group, or a tert-butyl group.

In the general formula (I), the "cycloalkyl group having 3 to 7 carbon atoms" represented by $R^6$ and $R^7$ includes the cycloalkyl group having 3 to 7 carbon atoms exemplified above, and is specifically preferably a cyclopropyl group, a cyclobutyl group, or a cyclopentyl group.

In the general formula (I), the "aromatic hydrocarbon group" represented by $R^6$ and $R^7$ includes the aromatic hydrocarbon group having 6 to 14 carbon atoms exemplified above, and is specifically preferably a phenyl group or a naphthyl group.

In the general formula (I), the "saturated heterocyclic group" represented by $R^6$ and $R^7$ includes the monocyclic or bicyclic 5- to 10-membered saturated heterocyclic group having 1 to 4 of any heteroatom of N, S, and O exemplified above.

In the general formula (I), the "unsaturated heterocyclic group" represented by $R^6$ and $R^7$ includes the monocyclic or bicyclic 5- to 10-membered unsaturated heterocyclic group having 1 to 4 of any heteroatom of N, S, and O exemplified above.

In the general formula (I), the "saturated heterocyclic group" formed when $R^6$ and $R^7$ are taken together with the nitrogen atom to which they are bound refers to a monocyclic or bicyclic saturated heterocyclic group having preferably 1 to 4 of any atom of oxygen atom, nitrogen atom, and sulfur atom. Examples thereof include pyrrolidinyl, piperidinyl, piperazinyl, hexamethyleneimino, morpholino, thiomorpholino, homopiperazinyl, tetrahydrofuranyl, and tetrahydropyranyl, groups.

$R^6$ and $R^7$ are the same or different and represent preferably a hydrogen atom; an alkyl group having 1 to 6 carbon atoms; a cycloalkyl group having 3 to 7 carbon atoms and optionally having a hydroxyl group; an aromatic hydrocarbon group; a saturated heterocyclic group; or an unsaturated heterocyclic group; represent more preferably a hydrogen atom, an alkyl group having 1 to 6 carbon atoms, or a cycloalkyl group having 3 to 7 carbon atoms and optionally having a hydroxyl group, and represent especially preferably a hydrogen atom, an alkyl group having 1 to 6 carbon atoms, or a cycloalkyl group having 3 to 7 carbon atoms.

Examples of the combination of $R^6$ and $R^7$ in the general formula (I) include preferably a combination where $R^6$ is a hydrogen atom, $R^7$ is a hydrogen atom, an alkyl group having 1 to 6 carbon atoms, or a cycloalkyl group having 3 to 7 carbon atoms and optionally having a hydroxyl group, and include more preferably a combination where $R^6$ is a hydrogen atom, $R^7$ is a hydrogen atom, an alkyl group having 1 to 6 carbon atoms, or a cycloalkyl group having 3 to 7 carbon atoms.

In the general formula (I), the "cycloalkyl group having 3 to 7 carbon atoms" represented by $R^8$ includes the cycloalkyl group having 3 to 7 carbon atoms exemplified above. Examples of the substituent in the cycloalkyl group are those exemplified above.

In the general formula (I), the "aromatic hydrocarbon group" represented by $R^8$ includes the aromatic hydrocarbon group having 6 to 14 carbon atoms exemplified above. Examples of the substituent in the aromatic hydrocarbon group are those exemplified above.

$R^8$ is preferably a cycloalkyl group having 3 to 7 carbon atoms or an aromatic hydrocarbon group having 6 to 14 carbon atoms.

The compound of the present invention is:
preferably a compound represented by the general formula (I) wherein X is CH or N; $Y^4$ is C—$R^3$ or N and $Y^1$ to $Y^3$ are CH, or $Y^2$ to $Y^4$ are CH and $Y^1$ is C—$R^3$; A and B are the same or different and represent an optionally substituted monocyclic unsaturated heterocyclic group having 1 to 4 heteroatoms selected from N, S and O; $R^1$ is a hydrogen atom; an alkyl group having 1 to 6 carbon atoms and optionally having a halogen atom; or a cycloalkyl group having 3 to 7 carbon atoms; $R^2$ is a cyano group or —CO—$R^4$, $R^4$ is an amino group, $R^3$ is a hydrogen atom, a halogen atom, an alkyl group having 1 to 6 carbon atoms, an alkoxy group having 1 to 6 carbon atoms, or —N($R^6$)($R^7$), and $R^6$ and $R^7$ represent a hydrogen atom; an alkyl group having 1 to 6 carbon atoms; a cycloalkyl group having 3 to 7 carbon atoms and optionally having a hydroxyl group; an aromatic hydrocarbon group; a saturated heterocyclic group; or an unsaturated heterocyclic group;

more preferably a compound represented by the general formula (I) wherein X is CH or N; $Y^4$ is C—$R^3$ or N and $Y^1$ to $Y^3$ are CH, or $Y^2$ to $Y^4$ are CH and $Y^1$ is C—$R^3$; A and B are the same or different and represent an optionally substituted monocyclic unsaturated heterocyclic group having 1 to 4 heteroatoms selected from N, S and O; $R^1$ is a hydrogen atom or an alkyl group having 1 to 6 carbon atoms and optionally having a halogen atom; $R^2$ is —CO—$R^4$; $R^4$ is an amino group; $R^3$ is a halogen atom, an alkyl group having 1 to 6 carbon atoms, or —N($R^6$)($R^7$); $R^6$ is a hydrogen atom; and $R^7$ is a hydrogen atom, an alkyl group having 1 to 6 carbon atoms, or a cycloalkyl group having 3 to 7 carbon atoms; and especially preferably a compound represented by the general formula (I) wherein X is CH or N; $Y^4$ is C—$R^3$ or N and $Y^1$ to $Y^3$ are CH, or $Y^2$ to $Y^4$ are CH and $Y^1$ is C—$R^3$; A is a monocyclic 5- to 6-membered unsaturated heterocyclic group having 1 to 3 heteroatoms selected from N, S, and O and optionally having an alkyl group with 1 to 6 carbon atoms; B is a monocyclic 5- to 6-membered unsaturated heterocyclic group having 1 to 3 heteroatoms selected from N, S, and O; $R^1$ is a hydrogen atom or an alkyl group having 1 to 6 carbon atoms and optionally having a halogen atom; $R^2$ is —CO—$R^4$; $R^4$ is an amino group; $R^3$ is a halogen atom, an alkyl group having 1 to 6 carbon atoms, or —N($R^6$)($R^7$); $R^6$ is a hydrogen atom; and $R^7$ is a hydrogen atom, an alkyl group having 1 to 6 carbon atoms, or a cycloalkyl group having 3 to 7 carbon atoms.

The compound of the present invention can be produced, for example, according to the following reaction scheme:

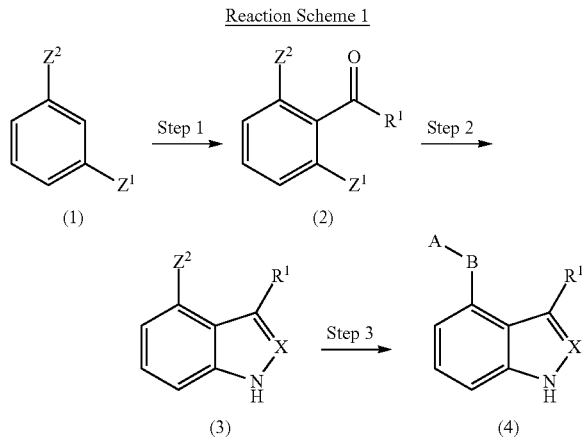

Reaction Scheme 1

In the above reaction scheme 1, $Z^1$ represents a halogen atom, $Z^2$ represents a hydrogen atom or a halogen atom, and X, $R^1$, A, and B have the same meanings as defined above.

<Step 1>

Step 1 comprises subjecting an easily obtainable compound represented by the general formula (1) to react with a metal reagent such as a lithium reagent, and then introducing thereto a carbonyl group corresponding to $R^1$.

Examples of the base used include lithium diisopropylamide, lithium bis(trimethylsilyl)amide, sodium bis(trimethylsilyl)amide, and potassium bis(trimethylsilyl)amide. The base is preferably lithium diisopropylamide and is preferably used in an amount of 1 to 2 equivalents. The reaction temperature is preferably −78 to 0° C., and the reaction time is preferably 10 minutes to 2 hours. An ether solvent (e.g., tetrahydrofuran (THF), diethyl ether, etc.) or a nonpolar solvent (e.g., benzene, toluene, etc.) can be used as a reaction solvent.

Subsequently, a carbonyl group corresponding to $R^1$ can be introduced thereto through reaction with an ester, amide or aldehyde form of $R^1$. When the aldehyde form of $R^1$ is used, the obtained hydroxyl form can be subjected to a usual method known in the art, for example, oxidation reaction with active manganese dioxide, to produce a carbonyl compound represented by the general formula (2).

<Step 2>

Step 2 comprises subjecting the compound represented by the general formula (2) to react with a hydrazine to produce an indazole compound represented by the general formula (3).

The hydrazine can be any of hydrazine, hydrazine hydrate and hydrazine hydrochloride and can be used in an amount of 1 to 30 equivalents. The reaction temperature is preferably 0° C. to the boiling point of a solvent used, and the reaction time is preferably 30 minutes to 50 hours. An alcoholic solvent (e.g., methanol, ethanol, isopropanol, etc.), an ether solvent (e.g., tetrahydrofuran, diisopropyl ether, etc.), an aprotic highly polar solvent (e.g., dimethylformamide, dimethylacetamide, dimethyl sulfoxide, etc.), or a mixed solvent thereof can be used as a reaction solvent.

<Step 3>

Step 3 comprises introducing a -B-A- group to an indole or indazole compound represented by the general formula (3) to produce an indole or indazole compound represented by the general formula (4).

The indole or indazole compound represented by the general formula (4) can be produced from the compound by the general formula (3) having a halogen atom represented by $Z^2$ by a Suzuki coupling method or by using an aromatic amine.

The Suzuki coupling method can be performed according to the method described in Chemical Review, 1995, 95, 2457-2483. Boronic acid or boronic acid ester corresponding to the -B-A- group can be synthesized by the usual method known in the art. When a halogen compound corresponding to the -B-A- group is easily available, the compound represented by the general formula (3) is converted to boronic acid or boronic acid ester, which can then be subjected to the Suzuki coupling method in the same way as above to produce an indole or indazole compound represented by the general formula (4).

Moreover, the reaction with an aromatic amine can be performed by reacting an aromatic amine such as imidazole or triazole with a halogen-substituted indazole represented by the general formula (3) through nucleophilic addition reaction for synthesis. This reaction can be usually carried out at a reaction temperature of room temperature to the boiling point of a solvent for a reaction time of 30 minutes to 50 hours using a nucleophilic reagent in an amount of 1 to 10 equivalents in the presence of a base. Moreover, the reaction can also be performed by the addition of a metal such as palladium, copper, etc.

The solvent used is not particularly limited as long as it is inert to this reaction. For example, an ether solvent (e.g., tetrahydrofuran, 1,2-dimethoxyethane and dioxane), an aprotic highly polar solvent (e.g., dimethylformamide, dimethylacetamide and dimethyl sulfoxide), or a mixed solvent thereof can be used.

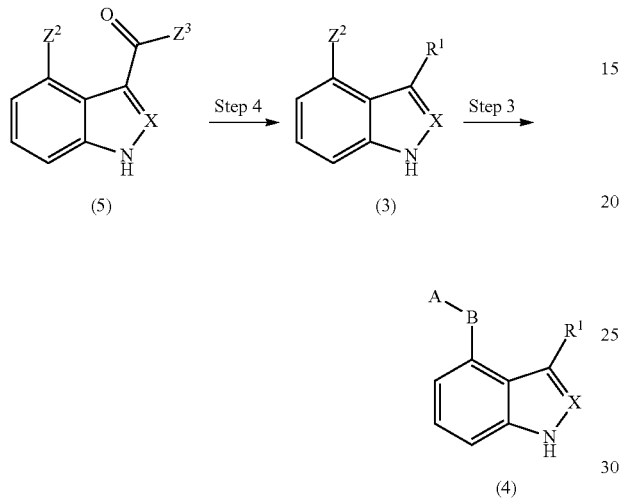

Reaction Scheme 2

In the reaction scheme 1, $Z^2$ represents a hydrogen atom or a halogen atom; $Z^3$ represents a hydrogen atom, an alkyl group, a cycloalkyl group, or an alkenyl group; and X, $R^1$, A, and B have the same meanings as defined above.

<Step 4>

Step 4 comprises converting the carbonyl group at the third position of an indole or indazole compound represented by the general formula (5) into an alkyl group or an alkenyl group.

The indole or indazole compound represented by the general formula (3) can be produced by reducing the carbonyl group or the alkenyl group into methylene with a reducing agent or derivatizing the carbonyl group into the alkenyl group by the Wittig reaction.

The reducing agent for the carbonyl group is preferably lithium aluminum hydride and used preferably in an amount of 3 to 4 equivalents. The reaction temperature is preferably 25° C. to 100° C. and an ether solvent (e.g., tetrahydrofuran (THF), diethyl ether, etc.) can be used as a reaction solvent. The reducing agent for the olefin is preferably performed by the hydrogenation reaction using a catalyst such as palladium or nickel. It is possible to use, for example, hydrogen, formic acid, cyclohexene as the reducing agent. An alcoholic solvent (e.g., methanol, ethanol, etc.) can be preferably used as a reaction solvent, the reaction temperature is preferably 25° C. to 100° C., and the reaction time is preferably 10 minutes to 2 hours.

Further, the Witting reaction can be carried out according to the method described in Chemical Reviews, 1989, 89, 863-927.

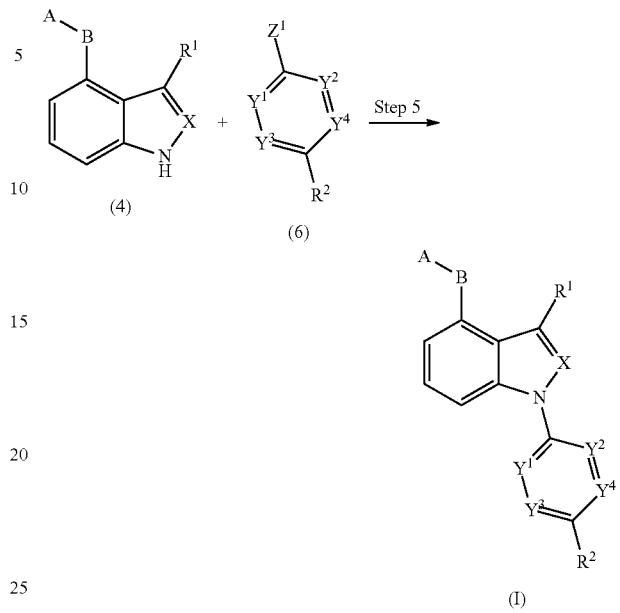

Reaction Scheme 3

In the reaction scheme 3, $Z^1$ represents an eliminable functional group such as, for example, a halogen atom, and X, $R^1$, $R^2$, $Y^1$, $Y^2$, $Y^3$, $Y^4$, A, and B have the same meanings as defined above.

<Step 5>

Step 5 comprises subjecting the nitrogen atom at position 1 of the indole or indazole compound represented by the general formula (4) to react with a halo-substituted phenyl, a halo-substituted pyridine, or a halo-substituted pyrimidine represented by the general formula (6) to obtain the compound represented by the general formula (I).

In this step, $Z^1$ in the compound represented by the general formula (6) can be any eliminable functional group. Examples thereof include a chlorine atom, a bromine atom, and a trifluoromethylsulfonyl group. Moreover, $R^2$ is preferably an electron-withdrawing group, and examples thereof include nitrile, ester, and nitro groups. The compound represented by the general formula (6) is easily available or can be synthesized, for example, according to the method described in Synthesis 1975, 502., J. Med. Chem. 1985, 1387-93.

The compound represented by the general formula (I) can be obtained by reacting 0.5 to 10 mol, preferably 0.8 to 2 mol of the compound represented by the general formula (6) with 1 mol of the compound represented by the general formula (4) at 0 to 180° C., preferably 20 to 150° C. in an appropriate solvent in the presence of 0.5 to 10 mol, preferably 0.8 to 2 mol of a base.

The solvent used is not particularly limited as long as it does not influence the reaction. Examples thereof include acetonitrile, tetrahydrofuran, dioxane, diethyl ether, diisopropyl ether, benzene, toluene, N,N-dimethylformamide, N,N-dimethylacetamide, N-methylpyrrolidone, and dimethyl sulfoxide. These solvents can be used alone or as a mixture. An inorganic base (e.g., lithium hydroxide, sodium hydroxide, potassium hydroxide, calcium hydroxide, barium hydroxide, lithium carbonate, sodium carbonate, potassium carbonate, and sodium hydride) or an organic base (e.g., pyridine, lutidine, collidine, 4-(N,N-dimethylamino)pyridine, triethylamine, diisopropylethylamine, 1,5-diazabicyclo[4.3.0]non-5-ene, and 1,8-diazabicyclo[5.4.0]undec-7-ene) can be used as the base.

When $Y^2$ and $Y^4$ in the general formula (I) are a carbon atom having a halogen atom, the halogen atom may be converted to, for example, amines, thioethers through the reaction with, for example, an amine, a thiol.

For the substituent such as a nitrile group, an ester group, or a nitro group represented by $R^2$ or for $R^3$ in any of $Y^1$, $Y^2$, $Y^3$ and $Y^4$, desired compounds can be produced by the usual method known in the art.

For example, when $R^2$ is a nitrile group, a carboxamide compound can be produced by the usual hydrolysis method known in the art. Moreover, when $R^2$ is an ester group, a carboxylic acid compound can be produced by hydrolysis of the ester and can further be reacted with an amine to produce the desired amide compound. When $R^2$ is a nitro group, an amine compound can be produced by, for example, catalytic reduction and can further be reacted with, for example, a carboxylic acid, an isocyanate to obtain, for example, the desired amide compound, urea compound. Moreover, for example, when $R^3$ is a halogen atom, the desired amine compound or thioether compound can be produced.

The compound of the present invention represented by the general formula (I) can also be obtained by reacting the compound represented by the general formula (3) with the compound represented by the general formula (6) according to the method of <Step 5> and converting the halogen atom represented by $Z^2$ to an aromatic amine according to the method of <Step 3>.

When introduction of a substituent or conversion of a functional group is carried out in the <Step 1> to <Step 5> described above and if there is a reactive substituent which causes reaction other than intended reactions, a protective group may be introduced to the reactive substituent in advance, as appropriate, by means known per se in the art, and the protective group may be removed by means known in the art after the intended reaction, to produce the target compound. After the completion of reaction, the compound of interest in each of these steps is collected from the reaction mixture according to the routine method. For example, the reaction mixture is appropriately neutralized, or insoluble materials, if any, are removed by filtration. Then, the reaction solution is extracted with a water-immiscible organic solvent such as toluene, ethyl acetate or chloroform, and the extracts are washed with, for example, water. Then, the organic layer containing the compound of interest is concentrated under reduced pressure, and the solvent is distilled off to obtain the compound of interest. The obtained compound of interest can be separated and purified, if necessary, by the routine method, for example, recrystallization, reprecipitation or a method generally used in the usual separation or purification of organic compounds (e.g., adsorption column chromatography using a carrier such as silica gel, alumina or magnesium-silica gel Florisil, partition column chromatography using a carrier such as Sephadex LH-20 (manufactured by Pharmacia), Amberlite XAD-11 (manufactured by Rohm and Haas Company) or Diaion HP-20 (manufactured by Mitsubishi Chemical Corp.), ion-exchange chromatography or normal- or reverse-phase column chromatography using a silica gel or alkylated silica gel, preferably, silica gel column chromatography). When the compound (I) is obtained in a free form, this free form can be converted to its pharmacologically acceptable salt by the method known per se in the art or a method equivalent thereto. While, when the compound (I) is obtained in a salt form, this salt can be converted to a free form or other salts of interest by the method known per se in the art or a method equivalent thereto.

When the compound (I) has isomers such as optical isomers, stereoisomers, regioisomers or rotational isomers, either of the isomers and a mixture thereof are both encompassed in the compound (I). For example, when the compound (I) has optical isomers, optical isomers resolved from racemates are also encompassed in the compound (I). Each of these isomers can be obtained as a single product by synthesis and separation (concentration, solvent extraction, column chromatography, recrystallization, etc.) approaches known per se in the art. The compound (I) may be crystalline. A single crystal form and a polymorphic mixture are both encompassed in the compound (I). These crystals can be produced by crystallizing the compound (I) using a crystallization method known per se in the art. The compound (I) may be a solvate (e.g., a hydrate) or a non-solvate. Both of them are encompassed in the compound (1).

A compound labeled with, for example, an isotope (e.g., 3H, 14C, 35S and 125I) is also encompassed in the compound (I).

A prodrug of the compound (I) or the salt thereof (hereinafter, abbreviated to the compound (I)) refers to a compound that is converted to the compound (I) through the reaction caused by, for example, an enzyme, gastric acid under physiological conditions in vivo, i.e., a compound that is converted to the compound (I) by enzymatic oxidation, reduction, hydrolysis etc., or a compound that is converted to the compound (I) by hydrolysis etc. caused by gastric acid etc. Moreover, the prodrug of the compound (I) can be any of those that are converted to the compound (I) under physiological conditions as described in "Pharmaceutical Research and Development" Vol. 7, Molecular Design, published in 1990 by Hirokawa-Shoten Ltd., p. 163-198.

The compound (I) of the present invention is useful as a drug such as an anticancer agent because it exhibits an excellent HSP90 inhibitory activity and an excellent cytostatic activity against cancer cells, and is highly safe due to the fact that the hERG inhibitory action which is an index of cardiac toxicity is weak. Moreover, the compound (I) of the present invention is highly soluble in water and can be administered orally. Thus, the compound (I) of the present invention is useful as an orally administrable drug such as an anticancer agent. Examples of malignant tumors include head and neck cancer, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, kidney cancer, bladder cancer, prostatic cancer, testicular tumor, osteosarcoma, soft-tissue sarcoma, leukemia, malignant lymphoma, multiple myeloma, skin cancer, brain tumor, and mesothelioma.

For using the compound (I) of the present invention as a drug, various dosage forms can be adopted according to the preventive or therapeutic purpose by mixing, as appropriate, the compound (I) with a pharmaceutically acceptable carrier. The forms can be any of, for example, oral formulations, injections, suppositories, ointments, and patches. Preferably, oral formulations are adopted. Each of these dosage forms can be produced by a general preparation method known to a person skilled in the art.

Various organic or inorganic carrier substances generally used as pharmaceutical materials are used as such a pharmaceutically acceptable carrier. Solid preparations are formulated using an excipient, a binder, a disintegrator, a lubricant and a coloring agent, and liquid preparations are formulated using, for example, a solvent, a solubilizer, a suspending agent, an isotonic agent, a buffer, a soothing agent. Moreover, pharmaceutical additives such as antiseptics, antioxidants, coloring agents, sweeteners, and stabilizers can also be used, if necessary.

When oral solid preparations are prepared, for example, an excipient and optionally an excipient, a binder, a disintegrator, a lubricant, a coloring agent, a corrigent are added, as appropriate, to the compound of the present invention, and then, for example, tablets, coated tablets, granules, powders, capsules, can be produced in a conventional manner.

When injections are prepared, for example, a pH adjuster, a buffer, a stabilizer, an isotonic agent, a local anesthetic are added to the compound of the present invention, and subcutaneous, intramuscular or intravenous injections can be produced in a conventional manner.

The amount of the compound of the present invention to be contained in each of these unit dosage forms varies depending on the conditions of a patient to which this formulation should be applied, or depending on the dosage form or the like. In general, the amount is preferably approximately 0.05 to 1000 mg for the oral formulation, approximately 0.01 to 500 mg for the injection, and approximately 1 to 1000 mg for the suppository, per unit dosage form.

Moreover, the daily dose of the drug having the dosage form differs depending on the conditions, body weight, age, sex, or the like of a patient and cannot be generalized. The daily dose in adult (body weight: 50 kg) can be usually approximately 0.05 to 5000 mg, preferably 0.1 to 1000 mg, which is preferably administered in one portion or in approximately two or three divided portions per day.

EXAMPLES

The present invention is specifically described below with reference to Examples and Test Examples, however, these Examples are described for the purpose of exemplifications only and do not limit the scope of the present invention.

Further, $^1$H-NMR spectra were measured using tetramethylsilane (TMS) as the internal standard, and chemical shifts are shown in δ values (ppm). The chemical shifts are each shown in parentheses by the number of protons, absorption pattern, and coupling constant (J value).

Moreover, in the absorption patterns, the following symbols are used: s=singlet, d=doublet, t=triplet, q=quartet, dd=double doublet, ddd=double double doublet, dt=double triplet, m=multiplet, br=broad, and br s=broad singlet.

In addition, in some structural formulae of compounds, the following symbols may be used: Me=methyl, Et=ethyl, tBu=tert-butyl, Ph=phenyl, Ac=acetyl, Boc=tert-butoxycarbonyl, TFA=trifluoroacetic acid, MsOH=methanesulfonic acid, DMF=dimethylformamide, THF=tetrahydrofuran, NMP=N-methylpyrrolidinone, and CDI=carbonyldiimidazole.

Example 1

2-(Tert-butylamino)-4-(3-isopropyl-4-(4-(pyridin-3-yl)-1H-imidazol-1-yl)-1H-indazol-1-yl)benzamide (1)

Example 1a

3-Isopropyl-4-(4-(pyridin-3-yl)-1H-imidazol-1-yl)-1H-indazole (1a)

A solution of diisopropylamine (9.64 mL) in THF (170 mL) was cooled to −78° C., and n-butyl lithium (23 mL) was added dropwise thereto under a nitrogen atmosphere. After 20 minutes, a solution of 1-bromo-3-fluorobenzene (10 g) in THF (85 mL) was added dropwise to the reaction solution at the same temperature, followed by stirring for 1 hour. Then, isobutyric anhydride (18 mL) was added thereto. After 15 minutes, the inner temperature was raised to 0° C. and hydrazine monohydrate (10 mL) was added thereto. After removal of the solvent by evaporation, ethylene glycol (200 mL) was added to the residue and the mixture was stirred overnight under heating at 100° C. After completion of the reaction, water was added to the reaction solution and the reaction solution was partitioned with ethyl acetate and water. The organic layer was washed with saturated brine and dried over anhydrous sodium sulfate. The solvent was evaporated off and the resulting residue was used in the subsequent reaction without purification.

The colorless oily substance (3 g) was added to N,N-dimethylformamide (DMF, 41 mL). The mixture was cooled to 0° C., and sodium hydride (602 mg) was added thereto under a nitrogen atmosphere. After stirring at the same temperature for 30 minutes, 4-methoxybenzyl chloride (2.05 mL) was added thereto and the mixture was stirred for 1 hour. After the reaction was stopped by the addition of water, the reaction solution was partitioned between ethyl acetate and water, and the organic layer was washed with saturated brine, and dried by the addition of anhydrous sodium sulfate. After removal of the solvent by evaporation, the residue was used in the subsequent reaction without further purification.

A solution of the colorless oily substance (4-bromo-3-(isopropyl)-1-(4-methoxybenzyl)-1H-indazole) (2.4 g), 3-(1H-imidazol-4-yl)pyridine hydrochloride (1.75 g), copper (I) oxide (96 mg), poly(ethylene glycol) (1.34 g), 8-quinolinol (194 mg), and cesium carbonate (8.7 g) in DMSO (22 mL) was stirred overnight under heating at 125° C. After completion of the reaction, the reaction solution was allowed to standing still for cooling, filtered, and the filtrate was partitioned between ethyl acetate and water. The organic layer was washed with saturated brine and dried by the addition of anhydrous sodium sulfate. After removal of the solvent by evaporation, the residue was purified by neutral silica gel column chromatography (chloroform/ethyl acetate/methanol) to obtain 3-isopropyl-1-(4-methoxybenzyl-4-(4-(pyridin-3-yl)-1H-imidazol-1-yl)-1H-indazole (710 mg, yield 250) as a yellow oily substance.

A solution of the yellow oily substance (710 mg) in trifluoroacetic acid (5.58 mL) and anisole (0.55 mL) was stirred under heating at 100° C. for 5 hours. After completion of the reaction, the solvent was evaporated and the residue was partitioned between chloroform and saturated aqueous sodium bicarbonate solution. The organic layer was washed with saturated brine, dried by the addition of anhydrous sodium sulfate. The solvent was evaporated and the residue was subjected to slurry washing with acetonitrile, thereby to obtain compound (1a) (397 mg, yield 78%) as a milky white solid.

Example 1b 2-(Tert-butylamino)-4-(3-isopropyl-4-(4-(pyridin-3-yl)-1H-imidazol-1-yl)-1H-indazol-1-yl)benzonitrile (1b)

A solution of compound (1a) (200 mg), copper(I) iodide (50 mg), cesium carbonate (430 mg), 4-bromo-2-(tert-butylamino)benzonitrile (250 mg), and N,N-dimethylethane-1,2-diamine (0.11 mL) in 1,4-dioxane (3.3 mL) was stirred overnight under heating at 150° C. After completion of the reaction, the reaction solution was allowed to standing still for cooling, filtered, and the filtrate was partitioned between ethyl acetate and water. The organic layer was washed with saturated brine and dried by the addition of anhydrous sodium sulfate. After removal of the solvent by evaporation, the residue was purified by neutral silica gel column chromatography (chloroform/ethyl acetate/methanol) to obtain compound (1b) (146 mg, yield 47%) as a white foamy substance.

Example 1c 2-(Tert-butylamino)-4-(3-isopropyl-4-(4-(pyridin-3-yl)-1H-imidazol-1-yl)-1H-indazol-1-yl)benzamide (1)

To a solution of compound (1b) in DMSO (4.41 mL) were added 4N aqueous sodium hydroxide solution (160 μL) and 30% aqueous hydrogen peroxide solution (60 μL), and the mixture was stirred at room temperature for 10 minutes. After completion of the reaction, water was poured into the reaction solution, and the precipitated solid was collected by filtration to obtain compound (1) (150 mg, yield 96%) as a white solid.

Example 2

5-(3-Isopropyl-4-(4-(pyridin-3-yl)-1H-imidazol-1-yl)-1H-indazol-1-yl)-2-pyridinecarboxyamide (2)

According to Example 1b, 5-(3-isopropyl-4-(4-(pyridin-3-yl)-1H-imidazol-1-yl)-1H-indazol-1-yl)-2-pyridinecarbonitrile (yield 16%) was obtained as a white foamy substance using 5-bromo-2-pyridinecarbonitrile in place of 4-bromo-2-(tert-butylamino)benzonitrile.

According to Example 1c, compound (2) (yield 63%) was obtained as a white solid using 5-(3-isopropyl-4-(4-(pyridin-3-yl)-1H-imidazol-1-yl)-1H-indazol-1-yl)-2-pyridinecarbonitrile in place of compound (1b).

Example 3

3-Chloro-4-(3-isopropyl-4-(4-pyridin-3-yl)-1H-imidazol-1-yl)-1H-indazol-1-yl)benzamide (3)

Example 3a

3-Chloro-4-(3-isopropyl-4-(4-pyridin-3-yl)-1H-imidazol-1-yl)-1H-indazol-1-yl)benzonitrile (3a)

A solution of compound (1a) (200 mg) in DMF (3.3 mL) was cooled to 0° C., and sodium hydride (32 mg) was added thereto under a nitrogen atmosphere. The mixture was stirred for 20 minutes. Then, 3-chloro-4-fluoro-benzonitrile (133 mg) was added, and the temperature was elevated to 50° C., followed by stirring for 30 minutes. After completion of the reaction, the reaction solution was allowed to standing still for cooling, water was added thereto, and the reaction solution was partitioned between ethyl acetate and water. The organic layer was washed with saturated brine and dried by the addition of anhydrous sodium sulfate. After removal of the solvent by evaporation, the residue was purified by neutral silica gel column chromatography (chloroform/ethyl acetate) to obtain compound (3a) (246 mg, yield 850) as a white foamy substance.

Example 3b

3-Chloro-4-(3-isopropyl-4-(4-(pyridin-3-yl)-1H-imidazol-1-yl)-1H-indazol-1-yl)benzamide (3)

According to Example 1c, compound (3) (133 mg, yield 52%) was obtained as a white solid using compound (3a) (246 mg) in place of compound (1b).

Example 4

4-(3-Isopropyl-4-(4-(pyridin-3-yl)-1H-imidazol-1-yl)-1H-indazol-1-yl)-3-methylbenzamide (4)

Example 4a 4-(3-Isopropyl-4-(4-(pyridin-3-yl)-1H-imidazol-1-yl)-1H-indazol-1-yl)-3-methylbenzonitrile (4a)

According to Example 1b, compound (4a) (yield 50%) was obtained as a white foamy substance using 4-bromo-3-methylbenzonitrile in place of 4-bromo-(2-tert-butylamino)benzonitrile.

Example 4b 4-(3-Isopropyl-4-(4-(pyridin-3-yl)-1H-imidazol-1-yl)-1H-indazol-1-yl)-3-methylbenzamide (4)

According to Example 1c, compound (4) (yield 85%) was obtained as a white solid using compound (4a) in place of compound (1b).

Example 5

3-Chloro-4-(3-isopropyl-4-(4-(1-methyl-1H-pyrazol-4-yl)-1H-imidazol-1-yl)-1H-indazol-1-yl)benzamide (5)

Example 5a

3-Isopropyl-4-(4-(1-methyl-1H-pyrazol-4-yl)-1H-imidazol-1-yl)-1H-indazole (5a)

According to Example 1a, compound (5a) (overall yield of three steps: 19%) was obtained as a milky white solid using 4-(1H-imidazol-4-yl)-1-methyl-1H-pyrazole hydrochloride in place of 3-(1H-imidazol-4-yl)pyridine hydrochloride.

Example 5b

3-Chloro-4-(3-isopropyl-4-(4-(1-methyl-1H-pyrazol-4-yl)-1H-imidazol-1-yl)-1H-indazol-1-yl)benzonitile (5b)

According to Example 3a, compound (5b) (yield 90%) was obtained as a white foamy substance using compound (5a) in place of compound (1a).

Example 5c

3-Chloro-4-(3-isopropyl-4-(4-(1-methyl-1H-pyrazol-4-yl)-1H-imidazol-1-yl)-1H-indazol-1-yl)benzamide (5)

According to Example 1c, compound (5) (yield 37%) was obtained as a white solid using compound (5b) in place of compound (1b).

Example 6

3-Ethyl-4-(3-isopropyl-4-(4-(1-methyl-1H-pyrazol-4-yl)-1H-imidazol-1-yl)-1H-indazol-1-yl)benzamide (6)

Example 6a

3-Ethyl-4-(3-isopropyl-4-(4-(1-methyl-1H-pyrazol-4-yl)-1H-imidazol-1-yl)-1H-indazol-1-yl)benzonitrile (6a)

Cesium carbonate (850 mg) was added to a solution of compound (5a) (200 mg) in DMSO (2.2 mL), and the mixture was heated to 130° C. The mixture was stirred for 10 minutes and 3-ethyl-4-fluorobenzonitrile (292 mg) was added thereto. The resulting mixture was stirred at the same temperature for 1.5 hours. After completion of the reaction, the reaction solution was allowed to standing still for cooling, and water was poured thereto. The reaction solution was partitioned between ethyl acetate and water. The organic layer was washed with saturated brine and dried by the addition of anhydrous sodium sulfate. After removal of the solvent by evaporation, the residue was purified by neutral silica gel column chromatography (chloroform/ethyl acetate/methanol) to obtain compound (6a) (151.8 mg, yield 54%) as a white foamy substance.

Example 6b

3-Ethyl-4-(3-isopropyl-4-(4-(1-methyl-1H-pyrazol-4-yl)-1H-imidazol-1-yl)-1H-indazol-1-yl)benzamide (6)

According to Example 1c, compound (6) (yield 48%) was obtained as a white solid using compound (6a) in place of compound (1b).

Example 7

5-(3-Isopropyl-4-(4-(1-methyl-1H-pyrazol-4-yl)-1H-imidazol-1-yl)-1H-indazol-1-yl)-2-pyridinecarboxyamide (7)

Example 7a 5-(3-Isopropyl-4-(4-(1-methyl-1H-pyrazol-4-yl)-1H-imidazol-1-yl)-1H-indazol-1-yl)-2-pyridinecarbonitrile (7a)

According to Example 1b, compound (7a) (yield 30%) was obtained as a white foamy substance using compound (5a) in place of compound (1a) and further using 5-bromo-2-pyridinecarbonitrile in place of 4-bromo-2-(tert-butylamino)benzonitrile.

Example 7b 5-(3-Isopropyl-4-(4-(1-methyl-1H-pyrazol-4-yl)-1H-imidazol-1-yl)-1H-indazol-1-yl)-2-pyridinecarboxyamide (7)

According to Example 1c, compound (7) (yield 45%) was obtained as a white solid using compound (7a) in place of compound (1b).

Example 8

4-(3-Isopropyl-4-(4-(1-methyl-1H-pyrazol-4-yl)-1H-imidazol-1-yl)-1H-indazol-1-yl)-3-methylbenzamide (8)

Example 8a 4-(3-Isopropyl-4-(4-(1-methyl-1H-pyrazol-4-yl)-1H-imidazol-1-yl)-1H-indazol-1-yl)-3-methylbenzonitrile (8a)

According to Example 1b, compound (8a) (yield 30%) was obtained as a white foamy substance using compound (5a) in place of compound (1a) and further using 4-bromo-3-methylbenzonitrile in place of 4-bromo-2-(tert-butylamino)benzonitrile.

Example 8b 4-(3-Isopropyl-4-(4-(1-methyl-1H-pyrazol-4-yl)-1H-imidazol-1-yl)-1H-indazol-1-yl)-3-methylbenzamide (8)

According to Example 1c, compound (8) (yield 69%) was obtained as a white solid using compound (8a) in place of compound (1b).

Example 9

2-(Tert-butylamino)-4-(3-isopropyl-4-(4-(1-methyl-1H-pyrazol-4-yl)-1H-imidazol-1-yl)-1H-indazol-1-yl)benzamide (9)

Example 9a 2-(Tert-butylamino)-4-(3-isopropyl-4-(4-(1-methyl-1H-pyrazol-4-yl)-1H-imidazol-1-yl)-1H-indazol-1-yl)benzonitrile (9a)

According to Example 1b, compound (9a) (yield 99%) was obtained as a white solid using compound (5a) in place of compound (1a).

Example 9b 2-(Tert-butylamino)-4-(3-isopropyl-4-(4-(1-methyl-1H-pyrazol-4-yl)-1H-imidazol-1-yl)-1H-indazol-1-yl)benzamide (9)

According to Example 1c, compound (9) (yield 57%) was obtained as a white solid using compound (9a) in place of compound (1b).

Example 10

4-(3-Isopropyl-4-(4-(pyridin-3-yl)-1H-imidazol-1-yl)-1H-indazol-1-yl)-3-(isopropylamino)benzamide (10)

Example 10a 4-(3-Isopropyl-4-(4-(pyridin-3-yl)-1H-imidazol-1-yl)-1H-indazol-1-yl)-3-nitrobenzonitrile (10a)

4-Chloro-3-nitrobenzonitrile (331 mg) and cesium carbonate (700 mg) were added to a solution of compound (1a) (500 mg) in acetonitrile (5.5 mL), and the mixture was stirred under heating at 70° C. for 4 hours. After completion of the reaction, the reaction solution was allowed to standing still for cooling and partitioned between ethyl acetate and water. The organic layer was washed with saturated brine and dried by the addition of anhydrous sodium sulfate. After removal of the solvent by evaporation, the residue was subjected to slurry washing (acetonitrile/methanol), thereby to obtain compound (10a) (470 mg, yield 64%) as a milky white solid.

Example 10b

3-Amino-4-(3-isopropyl-4-(4-(pyridin-3-yl)-1H-imidazol-1-yl)-1H-indazol-1-yl)benzonitrile (10b)

A solution of compound (10a) (470 mg), iron powder (584 mg) and ammonium chloride (470 mg) in THF (3.5 mL), methanol (3.5 mL) and water (3.5 mL) was stirred under heating at 80° C. for 2 hours. After completion of the reaction, the reaction solution was allowed to standing still for cooling, filtered, and the filtrate was concentrated. Water was added to the obtained residue to precipitate a solid, which was collected by filtration and dried to obtain compound (10b) (390 mg, yield 89%) as a milky white solid.

Example 10c 4-(3-Isopropyl-4-(4-(pyridin-3-yl)-1H-imidazol-1-yl)-1H-indazol-1-yl)-3-(isopropylamino)benzonitrile (10c)

Sodium triacetoxyborohydride (192 mg) was added to a solution of compound (10b) (190 mg) in dichloromethane (2.7 mL), and the mixture was cooled to 0° C. Then trifluoroacetic acid (0.45 mL) and acetone (67 μL) were added thereto and the mixture was stirred at the same temperature for 30 minutes. After completion of the reaction, the reaction solution was partitioned between ethyl acetate and saturated aqueous sodium hydrogen carbonate solution. The organic layer was washed with saturated brine and dried by the addition of anhydrous sodium sulfate. After removal of the solvent by evaporation, the residue was purified by neutral silica gel column chromatography (chloroform/methanol) to obtain compound (10c) (208.6 mg, yield 990) as a white foamy substance.

Example 10d 4-(3-Isopropyl-4-(4-(pyridin-3-yl)-1H-imidazol-1-yl)-1H-indazol-1-yl)-3-(isopropylamino)benzamide (10)

According to Example 1c, compound (10) (yield 75%) was obtained as a white solid using compound (10c) in place of compound (1b).

Example 11

3-(Cyclobutylamino)-4-(3-isopropyl-4-(4-(pyridin-3-yl)-1H-imidazol-1-yl)-1H-indazol-1-yl)benzamide (11)

Example 11a 3-(Cyclobutylamino)-4-(3-isopropyl-4-(4-(pyridin-3-yl)-1H-imidazol-1-yl)-1H-indazol-1-yl)benzonitrile (11a)

According to Example 10c, compound (11a) (yield 95%) was obtained as a white foamy substance using cyclobutanone in place of acetone.

Example 11b 3-(Cyclobutylamino)-4-(3-isopropyl-4-(4-(pyridin-3-yl)-1H-imidazol-1-yl)-1H-indazol-1-yl)benzamide (11)

According to Example 1c, compound (11) (yield 93%) was obtained as a white solid using compound (11a) in place of compound (1b).

Example 12

4-(3-Isopropyl-4-(4-(1-methyl-1H-pyrazol-4-yl)-1H-imidazol-1-yl)-1H-indazol-1-yl)-3-(isopropylamino)benzamide (12)

Example 12a 4-(3-Isopropyl-4-(4-(1-methyl-1H-pyrazol-4-yl)-1H-imidazol-1-yl)-1H-indazol-1-yl)-3-(isopropylamino)benonitrile (12a)

According to Example 10a, 4-(3-isopropyl-4-(4-(1-methyl-1H-pyrazol-4-yl)-1H-imidazol-1-yl)-1H-indazol-1-yl)-3-nitrobenzonitrile (yield 61%) was obtained as a milky white solid using compound (5a) in place of compound (1a).

According to Example 10b, 3-amino-4-(3-isopropyl-4-(4-(1-methyl-1H-pyrazol-4-yl)-1H-imidazol-1-yl)-1H-indazol-1-yl)benzonitrile (yield 93%) was obtained as a milky white solid using 4-(3-isopropyl-4-(4-(1-methyl-1H-pyrazol-4-yl)-1H-imidazol-1-yl) 1H-indazol-1-yl)-3-nitrobenzonitrile in place of compound (10a).

According to Example 10c, 4-(3-isopropyl-4-(4-(1-methyl-1H-pyrazol-4-yl)-1H-imidazol-1-yl) 1H-indazol-1-yl)-3-(isopropylamino)benzonitrile (yield 84%) was obtained as a white foamy substance using 3-amino-4-(3-isopropyl-4-(4-(1-methyl-1H-pyrazol-4-yl)-1H-imidazol-1-yl)-1H-indazol-1-yl)benzonitrile in place of compound (10b).

Example 12b 4-(3-Isopropyl-4-(4-(1-methyl-1H-pyrazol-4-yl)-1H-imidazol-1-yl) 1H-indazol-1-yl)-3-(isopropylamino)benzamide (12)

According to Example 1c, compound (12) (yield 81%) was obtained as a white solid using compound (12c) in place of compound (1b).

Example 13

3-(Cyclobutylamino)-4-(3-Isopropyl-4-(4-(1-methyl-1H-pyrazol-4-yl)-1H-imidazol-1-yl)-1H-indazol-1-yl)benzamide (13)

According to Example 12a, 3-(cyclobutylamino)-4-(3-isopropyl-4-(4-(1-methyl-1H-pyrazol-4-yl)-1H-imidazol-1-yl)-1H-indazol-1-yl)benzonitrile (yield 88%) was obtained as a white foamy substance using cyclobutanone in place of acetone.

According to Example 1c, compound (13) (yield 82%) was obtained as a white solid using 3-(cyclobutylamino)-4-(3-isopropyl-4-(4-(1-methyl-1H-pyrazol-4-yl)-1H-imidazol-1-yl)-1H-indazol-1-yl)benzonitrile in place of compound (1b).

Example 14

2-(Tert-butylamino)-4-(4-(4-(1-methyl-1H-pyrazol-4-yl)-1H-imidazol-1-yl)-3-(trifluoromethyl)-1H-indazol-1-yl)benzamide (14)

Example 14a

4-(4-(1-Methyl-1H-pyrazol-4-yl)-1H-imidazol-1-yl)-3-(trifluoromethyl)-1H-indazole (14a)

A solution of diisopropylamine (15.4 mL) in THF (130 mL) was cooled to −78° C. and n-butyl lithium (38 mL) was added dropwise to the solution under a nitrogen atmosphere. After 20 minutes, a solution of 1-bromo-3-fluorobenzene (15.4 g) in THF (80 mL) was added dropwise thereto at the same temperature and the mixture was stirred for 1 hour. Then, a solution of ethyl trifluoroacetate (12.6 mL) in THF (50 mL) was added thereto and the mixture was stirred at the same temperature for 1 hour. After completion of the reaction, water was added to the reaction solution and this was partitioned between ethyl acetate and water. The organic layer was washed with saturated brine and dried over anhydrous sodium sulfate. The solvent was removed by evaporation and the residue was used in the subsequent reaction without further purification.

Hydrazine monohydrate (25 mL) was added to a solution of the above colorless oily substance in ethanol (250 mL), and the mixture was stirred overnight under heating at 90° C. After completion of the reaction, water was added to the reaction solution and the mixture was partitioned between ethyl acetate and water. The organic layer was washed with saturated brine and dried by the addition of anhydrous sodium sulfate. After removal of the solvent by evaporation, the residue was used in the subsequent reaction without further purification.

Sodium hydride (485 mg) was added to a solution of the above colorless oily substance (2.27 g) in DMF (25.6 mL) under a nitrogen atmosphere, and the mixture was stirred at the same temperature for 15 minutes. Then, 4-methoxybenzyl chloride (1.34 mL) was added thereto and the temperature was elevated to room temperature, followed by stirring for 1 hour. After completion of the reaction, the reaction solution was partitioned between ethyl acetate and saturated aqueous sodium hydrogen carbonate solution, and the organic layer was washed with saturated brine and dried by the addition of anhydrous sodium sulfate. After removal of the solvent by evaporation, the residue was purified by neutral silica gel column chromatography (hexane/ethyl acetate) to obtain 4-bromo-1-(4-methoxybenzyl)-3-(trifluoromethyl)-1H-indazole (3.1 g, 75%) as a yellow oily substance. According to Example 1a, compound (14a) (400 mg, overall yield of three stages: 15%) was obtained as a milky white solid using 4-bromo-1-(4-methoxybenzyl)-3-(trifluoromethyl)-1H-indazole in place of 4-bromo-3-(isopropyl)-1-(4-methoxybenzyl)-1H-indazole and further using 4-(1H-imidazol-4-yl)-1-methyl-1H-pyrazole hydrochloride in place of 3-(1H-imidazol-4-yl)pyridine hydrochloride.

Example 14b

2-(Tert-butylamino)-4-(4-(4-(1-methyl-1H-pyrazol-4-yl)-1H-imidazol-1-yl)-3-(trifluoromethyl)-1H-indazol-1-yl)benzamide (14)

According to Example 1b, compound (14b) was obtained as a milky white solid using compound (14a) in place of compound (1a). The milky white solid was used in the subsequent reaction without further purification.

According to Example 1c, compound (14) (overall yield of two stages: 76%) was obtained as a white solid using compound (14b) in place of compound (1b).

Example 15

2-(Ethylamino)-4-(4-(4-(1-methyl-1H-pyrazol-4-yl)-1H-imidazol-1-yl)-3-(trifluoromethyl)-1H-indazol-1-yl)benzamide (15)

According to Example 1b, 2-(ethylamino)-4-(4-(4-(1-methyl-1H-pyrazol-4-yl)-1H-imidazol-1-yl)-3-(trifluoromethyl)-1H-indazol-1-yl)benzonitrile was obtained as a milky white solid using compound (14a) in place of compound (1a) and further using 4-bromo-2-(ethylamino)benzonitrile in place of 4-bromo-2-(tert-butylamino)benzonitrile. The milky white solid was used in the subsequent reaction without further purification.

According to Example 1c, compound (15) (overall yield of two stages: 92%) was obtained as a white solid using 2-(ethylamino)-4-(4-(4-(1-methyl-1H-pyrazol-4-yl)-1H-imidazol-1-yl)-3-(trifluoromethyl)-1H-indazol-1-yl)benzonitrile in place of compound (1b).

Example 16

2-(Tert-butylamino)-4-(4-(4-(pyridin-3-yl)-1H-imidazol-1-yl)-3-(trifluoromethyl)-1H-indazol-1-yl)benzamide (16)

Example 16a

4-(4-(pyridin-3-yl)-1H-imidazol-1-yl)-3-(trifluoromethyl)-1H-indazole (16a)

According to Example 14a, compound (16a) (overall yield of two stages: 7%) was obtained as a milky white solid using 3-(1H-imidazol-4-yl)pyridine hydrochloride in place of 4-(1H-imidazol-4-yl)-1-methyl-1H-pyrazole hydrochloride.

Example 16b

2-(Tert-butylamino)-4-(4-(4-(pyridin-3-yl)-1H-imidazol-1-yl)-3-(trifluoromethyl)-1H-indazol-1-yl)benzamide (16)

According to Example 1b, 2-(tert-butylamino)-4-(4-(4-(pyridin-3-yl)-1H-imidazol-1-yl)-3-(trifluoromethyl)-1H-indazol-1-yl)benzonitrile was obtained as a milky white solid using compound (16a) in place of compound (1a). The milky white solid was used in the subsequent reaction without further purification.

According to Example 1c, compound (16) (overall yield of two stages: 99%) was obtained as a white solid using 2-(tert-butylamino)-4-(4-(4-(pyridin-3-yl)-1H-imidazol-1-yl)-3-(trifluoromethyl)-1H-indazol-1-yl)benzonitrile in place of compound (1b).

Example 17

3-Methyl-4-(4-(4-(pyridin-3-yl)-1H-imidazol-1-yl)-3-(trifluoromethyl)-1H-indazol-1-yl)benzamide (17)

According to Example 1b, 3-methyl-4-(4-(4-(pyridin-3-yl)-1H-imidazol-1-yl)-3-(trifluoromethyl)-1H-indazol-1-yl)benzonitrile was obtained as a milky white solid using compound (16a) in place of compound (1a) and further using 4-fluoro-3-methylbenzonitrile in place of 4-bromo-2-(tert-butylamino)benzonitrile. The milky white solid was used in the subsequent reaction without further purification.

According to Example 1c, compound (17) (overall yield of two stages: 36%) was obtained as a white solid using 3-methyl-4-(4-(4-(pyridin-3-yl)-1H-imidazol-1-yl)-3-(trifluoromethyl)-1H-indazol-1-yl)benzonitrile in place of compound (1b).

Example 18

3-Ethyl-4-(4-(4-(1-methyl-1H-pyrazol-4-yl)-1H-imidazol-1-yl)-3-(trifluoromethyl)-1H-indazol-1-yl)benzamide (18)

According to Example 1b, 3-ethyl-4-(4-(4-(1-methyl-1H-pyrazol-4-yl)-1H-imidazol-1-yl)-3-(trifluoromethyl)-1H-indazol-1-yl)benzonitrile was obtained as a milky white solid using compound (14a) in place of compound (1a) and further using 3-ethyl-4-fluorobenzonitrile in place of 4-bromo-2-(tert-butylamino)benzonitrile. The milky white solid was used in the subsequent reaction without further purification.

According to Example 1c, compound (18) (overall yield of two stages: 19%) was obtained as a white solid using 3-ethyl-4-(4-(4-(1-methyl-1H-pyrazol-4-yl)-1H-imidazol-1-yl)-3-(trifluoromethyl)-1H-indazol-1-yl)benzonitrile in place of compound (1b).

Example 19

3-Ethyl-4-(4-(4-(pyridin-3-yl)-1H-imidazol-1-yl)-3-(trifluoromethyl)-1H-indazol-1-yl)benzamide (19)

According to Example 1b, 3-ethyl-4-(4-(4-(pyridin-3-yl)-1H-imidazol-1-yl)-3-(trifluoromethyl)-1H-indazol-1-yl)benzonitrile was obtained as a milky white solid using compound (16a) in place of compound (1a) and further using 3-ethyl-4-fluorobenzonitrile in place of 4-bromo-2-(tert-butylamino)benzonitrile. The milky white solid was used in the subsequent reaction without further purification.

According to Example 1c, compound (19) (overall yield of two stages: 23%) was obtained as a white solid using 3-ethyl-4-(4-(4-(pyridin-3-yl)-1H-imidazol-1-yl)-3-(trifluoromethyl)-1H-indazol-1-yl)benzonitrile in place of compound (1b).

Example 20

3-(Isopropylamino)-4-(4-(4-(1-methyl-1H-pyrazol-4-yl)-1H-imidazol-1-yl)-3-(trifluoromethyl)-1H-indazol-1-yl)benzamide (20)

Example 20a

3-Amino-4-(4-(4-(1-methyl-1H-pyrazol-4-yl)-1H-imidazol-1-yl)-3-(trifluoromethyl)-1H-indazol-1-yl)benzonitrile (20a)

According to Example 10a, 4-(4-(4-(1-methyl-1H-pyrazol-4-yl)-1H-imidazol-1-yl)-3-(trifluoromethyl)-1H-indazol-1-yl)-3-nitrobenzonitrile (yield 90%) was obtained as a milky white solid using compound (14a) in place of compound (1a).

According to Example 10b, compound (20a) (yield 93%) was obtained as a milky white solid using 4-(4-(4-(1-methyl-1H-pyrazol-4-yl)-1H-imidazol-1-yl)-3-(trifluoromethyl)-1H-indazol-1-yl)-3-nitrobenzonitrile in place of compound (10a).

Example 20b 3-(Isopropylamino)-4-(4-(4-(1-methyl-1H-pyrazol-4-yl)-1H-imidazol-1-yl)-3-(trifluoromethyl)-1H-indazol-1-yl)benzamide (20)

According to Example 10c, 3-(isopropylamino)-4-(4-(4-(1-methyl-1H-pyrazol-4-yl)-1H-imidazol-1-yl)-3-(trifluoromethyl)-1H-indazol-1-yl)benzonitrile was obtained as a milky white solid using compound (20b) in place of compound (10b). The milky white solid was used in the subsequent reaction without further purification.

According to Example 1c, compound (20) (overall yield of two stages: 94%) was obtained as a white solid using 3-(isopropylamino)-4-(4-(4-(1-methyl-1H-pyrazol-4-yl)-1H-imidazol-1-yl)-3-(trifluoromethyl)-1H-indazol-1-yl)benzonitrile in place of compound (1b).

Example 21

3-(Cyclobutylamino)-4-(4-(4-(1-methyl-1H-pyrazol-4-yl)-1H-imidazol-1-yl)-3-(trifluoromethyl)-1H-indazol-1-yl)benzamide (21)

According to Example 10c, 3-(cyclobutylamino)-4-(4-(4-(1-methyl-1H-pyrazol-4-yl)-1H-imidazol-1-yl)-3-(trifluoromethyl)-1H-indazol-1-yl)benzonitrile was obtained as a milky white solid using compound (20b) in place of compound (10b) and further using cyclobutanone in place of acetone. The milky white solid was used in the subsequent reaction without further purification.

According to Example 1c, compound (21) (overall yield of two stages: 96%) was obtained as a white solid using 3-(cyclobutylamino)-4-(4-(4-(1-methyl-1H-pyrazol-4-yl)-1H-imidazol-1-yl)-3-(trifluoromethyl)-1H-indazol-1-yl)benzonitrile in place of compound (1b).

Example 22

3-(Isopropylamino)-4-(4-(4-(pyridin-3-yl)-1H-imidazol-1-yl)-3-(trifluoromethyl)-1H-indazol-1-yl)benzamide (22)

Example 22a

3-Amino-4-(4-(4-(pyridin-3-yl)-1H-imidazol-1-yl)-3-(trifluoromethyl)-1H-indazol-1-yl)benzonitrile (22a)

According to Example 10a, 3-nitro-4-(4-(4-(pyridin-3-yl)-1H-imidazol-1-yl)-3-(trifluoromethyl)-1H-indazol-1-yl)benzonitrile was obtained as a milky white solid using compound (16a) in place of compound (1a). The milky white solid was used in the subsequent reaction without further purification.

According to Example 10b, compound (22b) (overall yield of two stages: 88%) was obtained as a milky white solid using 3-nitro-4-(4-(4-(pyridin-3-yl)-1H-imidazol-1-yl)-3-(trifluoromethyl)-1H-indazol-1-yl)benzonitrile in place of compound (10a).

Example 22b 3-(Isopropylamino)-4-(4-(4-(pyridin-3-yl)-1H-imidazol-1-yl)-3-(trifluoromethyl)-1H-indazol-1-yl)benzamide (22)

According to Example 10c, 3-(isopropylamino)-4-(4-(4-(pyridin-3-yl)-1H-imidazol-1-yl)-3-(trifluoromethyl)-1H-indazol-1-yl)benzonitrile was obtained as a milky white solid using compound (22b) in place of compound (10b). The milky white solid was used in the subsequent reaction without further purification.

According to Example 1c, compound (22) (overall yield of two stages: 96%) was obtained as a white solid using 3-(isopropylamino)-4-(4-(4-(pyridin-3-yl)-1H-imidazol-1-yl)-3-(trifluoromethyl)-1H-indazol-1-yl)benzonitrile in place of compound (1b).

Example 23

3-(Cyclobutylamino)-4-(4-(4-(pyridin-3-yl)-1H-imidazol-1-yl)-3-(trifluoromethyl)-1H-indazol-1-yl)benzamide (23)

According to Example 10c, 3-(cyclobutylamino)-4-(4-(4-(pyridin-3-yl)-1H-imidazol-1-yl)-3-(trifluoromethyl)-1H-indazol-1-yl)benzonitrile was obtained as a milky white solid using compound (22a) in place of compound (10b). The milky white solid was used in the subsequent reaction without further purification. According to Example 1c, compound (23) (yield 93%) was obtained as a white solid using 3-(cyclobutylamino)-4-(4-(4-(pyridin-3-yl)-1H-imidazol-1-yl)-3-(trifluoromethyl)-1H-indazol-1-yl)benzonitrile in place of compound (1b).

Example 24

3-Amino-4-(4-(4-(1-methyl-1H-pyrazol-4-yl)-1H-imidazol-1-yl)-3-(trifluoromethyl)-1H-indazol-1-yl)benzamide (24)

To a solution of compound (20a) (50 mg) in DMSO (0.5 mL) were added 4N aqueous sodium hydroxide solution (56 µL) and aqueous hydrogen peroxide solution (25 µL), and the mixture was stirred at room temperature for 10 minutes. After completion of the reaction, an aqueous ammonium chloride solution was added to the reaction solution, and then the mixture was partitioned with ethyl acetate. The organic layer was washed with saturated brine and dried by the addition of anhydrous sodium sulfate. After removal of the solvent by evaporation, the residue was subjected to slurry washing with acetonitrile. The precipitated solid was collected by filtration and dried to obtain compound (24) (33 mg, yield 63%) as a milky white solid.

Example 25

3-Amino-4-(4-(4-(pyridin-3-yl)-1H-imidazol-1-yl)-3-(trifluoromethyl)-1H-indazol-1-yl)benzamide (25)

According to Example 24, compound (25) (yield 65%) was obtained as a milky white solid using compound (22a) in place of compound (20a).

Example 26

3-Methyl-4-{4-(4-(1-methyl-1H-pyrazolo-4-yl)-1H-imidazolo-1-yl}-1H-indol-1-yl)benzamide (26)

Example 26a

4-Bromo-1-{(2-trimethylsilyl)ethoxy)methoxy}-1H-indole (26a)

4-Bromo-1H-indole (5.25 g) was dissolved in dimethylformamide (75 mL), and sodium hydride (1.40 g) was added thereto under ice-cooling. After stirring at 0° C. for 15 minutes, 2-(trimethylsilyl)ethoxymethyl chloride (5.17 mL) was added thereto. The reaction solution was stirred under heating at 70° C. for 30 minutes, partitioned between ethyl acetate and saturated aqueous sodium hydrogen carbonate solution, and the organic layer was washed with saturated brine and dried over anhydrous sodium sulfate. After removal of the solvent by evaporation, the residue was purified by neutral silica gel column chromatography (hexane/ethyl acetate) to obtain compound (26a) (7.74 g, 89%) as a colorless oily substance.

Example 26b

4-{4-(1-Methyl-1H-pyrazolo-4-yl)-1H-imidazolo-1-yl}-1H-indole (26b)

Compound (26a) (4.00 g), 4-(1-methyl-1H-pyrazolo-4-yl)-1H-imidazole dihydrochloride (2.72 g), copper(I) oxide (44 mg), N,N'-dimethylethylenediamine (97 µl), cesium carbonate (10.4 g), and polyethylene glycol (2.45 g) were suspended in dimethyl sulfoxide (12.5 mL), and the suspension was stirred at 150° C. for 24 hours. The reaction solution was partitioned between ethyl acetate and saturated aqueous ammonium chloride solution. The organic layer was washed with saturated brine and dried over anhydrous sodium sulfate. The solvent was removed by evaporation to obtain 4-{4-(1-methyl-1H-pyrazolo-4-yl)-1H-imidazolo-1-yl}-1-{(2-(trimethylsilyl)ethoxy)methoxy}-1H-indole, which was used in the subsequent reaction without further purification. The 4-{4-(1-methyl-1H-pyrazolo-4-yl)-1H-imidazolo-1-yl}-1-{(2-(trimethylsilyl)ethoxy)methoxy}-1H-indole was dissolved in tetrabutylammonium fluoride (1.0 M THF solution) (25 mL) and the resulting solution was heated at reflux for 48 hours. The reaction solution was partitioned between ethyl acetate and saturated aqueous ammonium chloride solution, and the organic layer was washed with saturated brine, followed by drying over anhydrous sodium sulfate. After removal of the solvent by evaporation, the residue was purified by neutral silica gel column chromatography (hexane/ethyl acetate) to obtain compound (26b) (1.00 g, 31%) as a brown solid.

Example 26c

3-Methyl-4-{4-(4-(1-methyl-1H-pyrazolo-4-yl)-1H-imidazolo-1-yl}-1H-indol-1-yl)benzamide (26)

Compound (26b) (50 mg), 4-fluoro-3-methylbenzonitrile (38 mg), and cesium carbonate (123 mg) were dissolved in dimethyl sulfoxide (1.0 mL), and the solution was stirred at 120° C. for 3 hours, after which time 4 M aqueous sodium hydroxide solution (70 µl) and 30% aqueous hydrogen peroxide solution were added thereto at room temperature, followed by stirring for 30 minutes. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (26) (35 mg, yield 47%) as a white solid.

Example 27

3-Ethyl-4-{4-(4-(1-methyl-1H-pyrazolo-4-yl)-1H-imidazolo-1-yl}-1H-indol-1-yl)benzamide (27)

According to Example 26c, compound (27) (58%) was obtained as a white solid using 3-ethyl-4-fluorobenzonitrile in place of 4-fluoro-3-methylbenzonitrile.

Example 28

3-Fluoro-4-{4-(4-(1-methyl-1H-pyrazolo-4-yl)-1H-imidazolo-1-yl}-1H-indol-1-yl)benzamide (28)

According to Example 26c, compound (28) (66%) was obtained as a white solid using 3,4-difluorobenzonitrile in place of 4-fluoro-3-methylbenzonitrile.

Example 29

3-Chloro-4-{4-(4-(1-methyl-1H-pyrazolo-4-yl)-1H-imidazolo-1-yl}-1H-indol-1-yl)benzamide (29)

According to Example 26c, compound (29) (42%) was obtained as a white solid using 3-chloro-4-fluorobenzonitrile in place of 4-fluoro-3-methylbenzonitrile.

Example 30

3-Bromo-4-{4-(4-(1-methyl-1H-pyrazolo-4-yl)-1H-imidazolo-1-yl}-1H-indol-1-yl)benzamide (30)

According to Example 26c, compound (30) (38%) was obtained as a white solid using 3-bromo-4-fluorobenzonitrile in place of 4-fluoro-3-methylbenzonitrile.

Example 31

3-Amino-4-[4-(4-(1-methyl-1H-pyrazolo-4-yl)-1H-imidazolo-1-yl]-1H-indol-1-yl)benzamide (31)

Example 31a

3-Amino-4-{4-(4-(1-methyl-1H-pyrazolo-4-yl)-1H-imidazolo-1-yl}-1H-indo1-1-yl)benzonitrile (31a)

Compound (26b) (200 mg), 4-chloro-3-nitrobenzonitrile (166 mg), and potassium carbonate (210 mg) were dissolved in dimethyl sulfoxide (2.3 mL), and the solution was stirred at 80° C. for 1 hour. The reaction solution was partitioned between ethyl acetate and water, and the organic layer was washed twice with water and dried over anhydrous sodium sulfate. The solvent was removed by evaporation to obtain 4-{4-(4-(1-methyl-1H-pyrazolo-4-yl)-1H-imidazolo-1-yl}-1H-indol-1-yl)-3-nitro-benzonitrile, which was used in the subsequent reaction without further purification. The obtained 4-{4-(4-(1-methyl-1H-pyrazolo-4-yl)-1H-imidazolo-1-yl}1 -1H-indo1-1-yl)-3-nitro-benzonitrile was dissolved in tetrahydrofuran (1.5 mL), methanol (1.5 mL) and 2 M HC1 (1.5mL), and iron powder (215 mg) was added thereto, followed by stirring at 80° C. for 2 hours. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (31a) (108 mg, 37%) as a brown solid.

Example 31b

3-Amino-4-[4-(4-(1-methyl-1H-pyrazolo-4-yl)-1H-imidazolo-1-yl]-1H-indol-1-yl)benzamide (31)

Compound (31a) (30 mg) was dissolved in dimethyl sulfoxide (0.4 mL), and 4 M aqueous sodium hydroxide solution (40 µl) and 30% aqueous hydrogen peroxide solution (14 ill) were added thereto, followed by stirring for 30 minutes. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (31) (13 mg, 41%) as a white solid.

Example 32

3-(Ethylamino)-4-{4-(4-(1-methyl-1H-pyrazolo-4-yl)-1H-imidazolo-1-yl}-1H-indol-1-yl)benzamide (32)

Compound (31a) (40 mg) and sodium triacetoxyborohydride (44 mg) were suspended in THF (0.52 mL), and acetaldehyde (12 µl) and acetic acid (0.1 mL) were added thereto, followed by stirring for 30 minutes. After adding methanol to the reaction solution, the reaction solution was partitioned between ethyl acetate and water, and the organic layer was washed twice with water and dried over anhydrous sodium sulfate. After removal of the solvent by evaporation, the residue was dissolved in dimethyl sulfoxide (0.4 mL), and 4 M aqueous sodium hydroxide solution (40 µl) and 30% aqueous hydrogen peroxide solution (14 µl) were added thereto, followed by stirring for 30 minutes. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (32) (21 mg, 47%) as a white solid.

Example 33

3-(Isopropylamino)-4-{4-(4-(1-methyl-1H-pyrazolo-4-yl)-1H-imidazolo-1-yl}-1H-indol-1-yl)benzamide (33)

According to Example 32, compound (33) (65%) was obtained as a white solid using acetone in place of acetaldehyde.

Example 34

2-(Ethylamino)-4-{4-(4-(1-methyl-1H-pyrazolo-4-yl)-1H-imidazolo-1-yl}-1H-indol-1-yl)benzamide (34)

Compound (26b) (50 mg), copper iodide (15 mg), N,N'-dimethylethylenediamine (32 µl), cesium carbonate (155 mg), and 4-bromo-2-(ethylamino)benzonitrile (51 mg) were suspended in 1,4-dioxan (1.0 mL), and the suspension was stirred at 150° C. for 24 hours. The reaction solution was partitioned between ethyl acetate and water, and the organic layer was dried over anhydrous sodium sulfate. After removal of the solvent by evaporation, the residue was dissolved in dimethyl sulfoxide (1.0 mL), and 4M aqueous sodium hydroxide solution (70 µl) and 30% aqueous hydrogen peroxide solution (64 µl) were added thereto, followed by stirring for 30 minutes. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (34) (33 mg, 40%) as a white solid.

Example 35

2-(Tert-butylamino)-4-{4-(4-(1-methyl-1H-pyrazolo-4-yl)-1H-imidazolo-1-yl}-1H-indol-1-yl)benzamide (35)

According to Example 34, compound (35) (54%) was obtained as a white solid using 4-bromo-2-(tert-butylamino)benzonitrile in place of 4-bromo-2-(ethylamino)benzonitrile.

Example 36

3-Methyl-4-{4-(4-(pyridin-3-yl)-1H-imidazolo-1-yl}-1H-indol-1-yl)benzamide (36)

Example 36a

4-{4-(Pyridin-3-yl)-1H-imidazolo-1-yl}-1H-indole (36a)

According to Example 26b, compound (36a) (18%) was obtained as a brown solid using 4-(pyridin-3-yl)-1H-imidazole dihydrochloride in place of 4-(1-methyl-1H-pyrazolo-4-yl)-1H-imidazole dihydrochloride.

Example 36b

3-Methyl-4-{4-(4-(pyridin-3-yl)-1H-imidazolo-1-yl})-1H-indol-1-yl}benzamide (36)

Compound (36a) (40 mg), 4-fluoro-3-methylbenzonitrile (25 mg), and potassium carbonate (52 mg) were dissolved in dimethyl sulfoxide (1.0 mL), and the solution was stirred at 120° C. for 3 hours. Then, 4 M aqueous sodium hydroxide solution (70 µl) and 30% aqueous hydrogen peroxide solution (35 µl) were added to the reaction solution at room temperature, and the mixture was stirred for 30 minutes. The reaction solution was partitioned between ethyl acetate and water, and the organic layer was washed twice with water and dried over anhydrous sodium sulfate. After removal of the solvent by evaporation, the residue was purified by neutral silica gel column chromatography (chloroform/methanol) to obtain compound (36) (57 mg, 95%) as a white solid.

Example 37

3-Ethyl-4-{4-(4-(pyridin-3-yl)-1H-imidazolo-1-yl)-1H-indol-1-yl}benzamide (37)

According to Example 36b, compound (37) (80%) was obtained as a white solid using 3-ethyl-4-fluorobenzonitrile in place of 4-fluoro-3-methylbenzonitrile.

Example 38

3-Fluoro-4-{4-(4-(pyridin-3-yl)-1H-imidazolo-1-yl)-1H-indol-1-yl}benzamide (38)

According to Example 36b, compound (38) (94%) was obtained as a white solid using 3,4-difluorobenzonitrile in place of 4-fluoro-3-methylbenzonitrile.

Example 39

3-Chloro-4-{4-(4-(pyridin-3-yl)-1H-imidazolo-1-yl)-1H-indol-1-yl}benzamide (39)

According to Example 36b, compound (39) (98%) was obtained as a white solid using 3-chloro-4-fluorobenzonitrile in place of 4-fluoro-3-methylbenzonitrile.

Example 40

3-Amino-4-{4-(4-(pyridin-3-yl)-1H-imidazolo-1-yl)-1H-indol-1-yl}benzamide (40)

Example 40a

3-Amino-4-{4-(4-(pyridin-3-yl)-1H-imidazolo-1-yl)-1H-indol-1-yl}benzonitrile (40a)

According to Example 31a, compound (40a) (89%) was obtained as a white solid using compound (36a) in place of compound (26b).

Example 40b

3-Amino-4-{4-(4-(pyridin-3-yl)-1H-imidazolo-1-yl)-1H-indol-1-yl}benzamide (40)

According to Example 31b, compound (40) (29%) was obtained as a white solid using compound (40a) in place of compound (31a).

Example 41

3-(Ethylamino)-4-{4-(4-(pyridin-3-yl)-1H-imidazolo-1-yl)-1H-indol-1-yl}benzamide (41)

According to Example 32, compound (41) (29%) was obtained as a white solid using compound (40a) in place of compound (31a).

Example 42

3-(Isopropylamino)-4-{4-(4-(pyridin-3-yl)-1H-imidazolo-1-yl)-1H-indol-1-yl}benzamide (42)

According to Example 33, compound (42) (71%) was obtained as a white solid using compound (40a) in place of compound (31a).

Example 43

2-(Ethylamino)-4-{4-(4-(pyridin-3-yl)-1H-imidazolo-1-yl)-1H-indol-1-yl}benzamide (43)

According to Example 34, compound (43) (89%) was obtained as a white solid using compound (36a) in place of compound (26b).

Example 44

2-(Tert-butylamino)-4-{4-(4-(pyridin-3-yl)-1H-imidazolo-1-yl)-1H-indol-1-yl}benzamide (44)

According to Example 35, compound (44) (86%) was obtained as a white solid using compound (36a) in place of compound (26b).

Example 45

3-Ethyl-4-{3-methyl-4-(4-(1-methyl-1H-pyrazolo-4-yl)-1H-imidazolo-1-yl)-1H-indol-1-yl}benzamide (45)

Example 45a

4-Bromo-1-(4-methoxybenzyl)-3-methyl-1H-indole (45a)

4-Bromo-3-methyl-1H-indole (1.33 g) was dissolved in dimethylformamide (20 mL), and sodium hydride (0.33 g) was added thereto under ice-cooling. After stirring at 0° C. for 15 minutes, p-methoxybenzyl chloride (0.95 mL) was added thereto. The reaction solution was stirred under heating at 70° C. for 30 minutes and partitioned between ethyl acetate and 1 M HCl aqueous solution. The organic layer was washed with saturated brine and dried over anhydrous sodium sulfate. After removal of the solvent by evaporation, the residue was purified by neutral silica gel column chromatography (hexane/ethyl acetate) to obtain compound (45a) (2.09 g, 99%) as a colorless oily substance.

Example 45b

3-Methyl-4-{4-(1-methyl-1H-pyrazolo-4-yl)-1H-imidazolo-1-yl}-1H-indole (45b)

Compound (45a) (1.04 g), 4-(1-methyl-1H-pyrazolo-4-yl)-1H-imidazole dihydrochloride (1.04 g), copper(I) oxide (45 mg), N,N'-dimethylethylenediamine (101 µl), and cesium carbonate (5.13 g) were suspended in dimethyl sulfoxide (6.3 mL), and the suspension was stirred at 150° C. for 12 hours. The reaction solution was partitioned between ethyl acetate and saturated aqueous ammonium chloride solution. The organic layer was washed with saturated brine and dried over anhydrous sodium sulfate. The solvent was removed by evaporation to obtain 3-methyl-4-{4-(1-methyl-1H-pyrazolo-4-yl)-1H-imidazolo-1-yl}-1-(4-methoxybenzyl)-1H-indole, which was used in the subsequent reaction without further purification. The 3-methyl-4-{4-(1-methyl-1H-pyrazolo-4-yl)-1H-imidazolo-1-yl}-1-(4-methoxybenzyl)-1H-indole was dissolved in anisole (2.0 mL) and trifluoroacetic acid (3.7 mL) and the resulting solution was heated at reflux for 48 hours. The reaction solution was partitioned between ethyl acetate and 2 M HCl aqueous solution, and the aqueous layer was neutralized with 5 M aqueous sodium hydroxide solution, and then extracted with chloroform. The organic layer was dried over anhydrous sodium sulfate and the solvent was removed by evaporation. Acetonitrile was added to the residue and the resulting precipitate was collected by filtration to obtain compound (45b) (0.2 g, 23%) as a white solid.

Example 45c

3-Ethyl-4-{3-methyl-4-(4-(1-methyl-1H-pyrazolo-4-yl)-1H-imidazolo-1-yl)-1H-indol-1-yl}benzamide (45)

According to Example 27, compound (45) (60%) was obtained as a white solid using compound (45b) in place of compound (26b).

Example 46

2-(Tert-butylamino)-4-{3-methyl-4-(4-(1-methyl-1H-pyrazolo-4-yl)-1H-imidazolo-1-yl)-1H-indol-1-yl}benzamide (46)

According to Example 35, compound (46) (77%) was obtained as a white solid using compound (45b) in place of compound (26b).

Example 47

2-(Tert-butylamino)-4-{3-methyl-4-(4-(pyridin-3-yl)-1H-imidazolo-1-yl)-1H-indol-1-yl}benzamide (47)

Example 47a

4-{4-Pyridin-3-yl)-1H-imidazolo-1-yl}-1H-indole (47a)

According to Example 45b, compound (47a) (28%) was obtained as a white solid using 4-(pyridin-3-yl)-1H-imidazole dihydrochloride in place of 4-(1-methyl-1H-pyrazolo-4-yl)-1H-imidazole dihydrochloride.

Example 47b 2-(Tert-butylamino)-4-{3-methyl-4-(4-(pyridin-3-yl)-1H-imidazolo-1-yl)-1H-indol-1-yl}benzamide (47)

According to Example 35, compound (47) (9%) was obtained as a white solid using compound (47a) in place of compound (26b).

Example 48

2-(Tert-butylamino)-4-{3-ethyl-4-(4-(1-methyl-1H-pyrazolo-4-yl)-1H-imidazolo-1-yl)-1H-indol-1-yl}benzamide (48)

Example 48a

4-Bromo-1-(4-methoxybenzyl)-1H-indol-3-carboaldehyde (48a)

According to Example 45a, compound (48a) (87%) was obtained as an oily substance using 4-bromo-1H-indole-3-carboaldehyde in place of 4-bromo-3-methyl-1H-indole.

Example 48b

4-Bromo-1-(4-methoxybenzyl)-3-vinyl-1H-indole (48b)

Methyltriphenylphosphonium bromide (1.14 g) was suspended in tetrahydrofuran (6.0 mL), and to this solution was added n-butyl lithium (in 2.64 M hexane solution of 1.16 mL) at −78° C. The mixture was stirred at 0° C. for 1 hour and then a solution of compound (48a) (0.91 g) in tetrahydrofuran (2.0 mL) was added thereto, followed by stirring at room temperature for 1 hour. The reaction solution was partitioned with ethyl acetate and water, and the organic layer was washed with saturated brine, dried over anhydrous sodium sulfate, and the solvent was removed by evaporation. The residue was purified by neutral silica gel column chromatography (hexane/ethyl acetate) to obtain compound (48b) (0.864 g, 95%) as a colorless oily substance.

Example 48c

3-Ethyl-4-{4-(1-methyl-1H-pyrazolo-4-yl)-1H-imidazolo-1-yl}-1H-indole (48c)

Compound (48b) (0.86 g), 4-(1-methyl-1H-pyrazolo-4-yl)-1H-imidazole dihydrochloride (0.83 g), copper(I) oxide (36 mg), N,N'-dimethylethylenediamine (66 µl), and cesium carbonate (4.09 g) were suspended in dimethyl sulfoxide (5.0 mL), and the suspension was stirred at 150° C. for 12 hours. The reaction solution was partitioned between ethyl acetate and saturated aqueous ammonium chloride solution. The organic layer was washed with saturated brine and dried over anhydrous sodium sulfate. The solvent was removed by evaporation to obtain 4-{4-(1-methyl-1H-pyrazolo-4-yl)-1H-imidazolo-1-yl}-1-(4-methoxybenzyl)-3-vinyl-1H-indole, which was used in the subsequent reaction without further purification. The 4-{4-(1-methyl-1H-pyrazolo-4-yl)-1H-imidazolo-1-yl}-1-(4-methoxybenzyl)-3-vinyl-1H-indole and palladium hydroxide (450 mg) were suspended in cyclohexene (2.0 mL) and ethanol (4.0 mL) and heated at reflux for 5 hours. The reaction solution was filtered and the solvent was removed by evaporation. The residue was dissolved in anisole (2.0 mL) and trifluoroacetic acid (3.7 mL), and the solution was heated at reflux for 48 hours. The reaction solution was partitioned between ethyl acetate and 2 M HCl aqueous solution, and the aqueous layer was neutralized with 5 M aqueous sodium hydroxide solution, and then extracted with chloroform. The organic layer was dried over anhydrous sodium sulfate and the solvent was removed by evaporation. Acetonitrile was added to the residue and the resulting precipitate was collected by filtration to obtain compound (48c) (0.05 g, 7%) as a brown solid.

Example 48d 2-(Tert-butylamino)-4-{3-ethyl-4-(4-(1-methyl-1H-pyrazolo-4-yl)-1H-imidazolo-1-yl)-1H-indol-1-yl}benzamide (48)

According to Example 35, compound (48) (63%) was obtained as a white solid using compound (48c) in place of compound (26b)

Example 49

3-Ethyl-4-{4-(4-(1-methyl-1H-pyrazolo-4-yl)-3-propyl-1H-imidazolo-1-yl)-1H-indol-1-yl}benzamide (49)

Example 49a (E)/(Z)-4-Bromo-1-(4-methoxybenzyl)-3-(prope-1-enyl)-1H-indole (49a)

According to Example 48b, compound (49a) (90%) was obtained as a colorless oily substance using ethyltriphenylphosphonium bromide in place of methyltriphenylphosphonium bromide.

Example 49b

4-{4-(1-methyl-1H-pyrazolo-4-yl)-1H-imidazolo-1-yl}-3-propyl-1H-indole (49b)

According to Example 48c, compound (49b) (43%) was obtained as a brown solid using compound (49a) in place of compound (48b).

Example 49c

3-Ethyl-4-{4-(4-(1-methyl-1H-pyrazolo-4-yl)-3-propyl-1H-imidazolo-1-yl)-1H-indol-1-yl}benzamide (49)

According to Example 27, compound (49) (58%) was obtained as a white solid using compound (49b) in place of compound (26b).

Example 50

2-(Tert-buylamino)-4-{4-(4-(1-methyl-1H-pyrazolo-4-yl)-1H-imidazolo-1-yl)-3-propyl-1H-indol-1-yl}benzamide (50)

According to Example 35, compound (50) (79%) was obtained as a white solid using compound (49b) in place of compound (26b).

Example 51

3-Ethyl-4-{3-isopropyl-4-(4-(1-methyl-1H-pyrazolo-4-yl)-1H-imidazolo-1-yl)-1H-indol-1-yl}benzamide (51)

Example 51a 1-(4-Bromo-1-(4-methoxybenzyl)-1H-indo-3-yl)ethanone (51a)

According to Example 45a, compound (51a) (85%) was obtained as a colorless oily substance using 1-(4-bromo-1H-indo-3-yl)ethanone in place of 4-bromo-3-methyl-1H-indole.

Example 51b

4-Bromo-1-(4-methoxybenzyl)-3-(prope-1-en-2-yl)-1H-indole (51b)

According to Example 48b, compound (51b) (90%) was obtained as a colorless oily substance using compound (51a) in place of compound (48a).

Example 51c

3-Isopropyl-4-{4-(1-methyl-1H-pyrazolo-4-yl)-1H-imidazolo-1-yl}-1H-indole (51c)

According to Example 48c, compound (51c) (10%) was obtained as a brown solid using compound (51b) in place of compound (48b).

Example 51d

3-Ethyl-4-{3-isopropyl-4-(4-(1-methyl-1H-pyrazolo-4-yl)-1H-imidazolo-1-yl)-1H-indol-1-yl}benzamide (51)

According to Example 27, compound (51) (57%) was obtained as a white solid using compound (51c) in place of compound (26b).

Example 52

2-(Tert-butylamino)-4-{3-isopropyl-4-(4-(1-methyl-1H-pyrazolo-4-yl)-1H-imidazolo-1-yl)-1H-indol-1-yl}benzamide (52)

According to Example 35, compound (52) (64%) was obtained as a white solid using compound (51c) in place of compound (26b).

In addition, the structural formulae and physical properties of the compounds synthesized in the above Examples are shown in the following Table.

TABLE 1

| Compound No. | Structural formula | Physical properties |
|---|---|---|
| 1 | (structure) | $^1$H-NMR (DMSO-d$_6$): δ 9.06 (1H, d, J = 2.7 Hz), 8.64 (1H, s), 8.42 (1H, dd, J = 5.4, 1.8 Hz), 8.25 (1H, d, J = 1.C8 Hz), 8.19-8.14 (2H, m), 7.91 (1H, d, J = 8.1 Hz), 7.77 (1H, d, J = 8.1 Hz), 7.60 (1H, t, J = 8.1 Hz), 7.39 (1H, dd, J = 8.1, 5.4 Hz), 7.30 (1H, d, J = 5.4 Hz), 7.13 (1H, d, J = 2.7 Hz), 6.87 (1H, dd, J = 8.1, 2.7 Hz), 2.79 (1H, q, J = 5.4 Hz), 1.35 (9H, s), 1.09 (6H, d, J = 5.4 Hz); LRMS (ESI) m/z 494 [M + H]$^+$. |

TABLE 1-continued
| Compound No. | Structural formula | Physical properties |
|---|---|---|
| 2 | 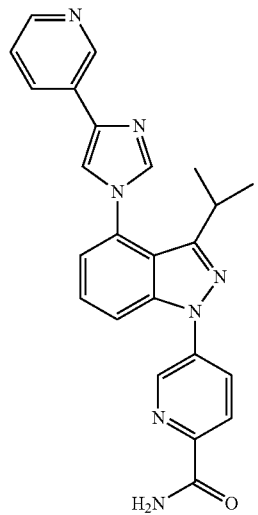 [SMILES: CC(C)c1nn(-c2ccc(C(N)=O)nc2)c2cccc(-n3cnc(-c4cccnc4)c3)c12] | $^1$H-NMR (DMSO-$d_6$): δ 9.09 (2H, dd, J = 2.7, 1.8 Hz), 8.46 (1H, dd, J = 5.4, 1.8 Hz), 8.41 (1H, dd, J = 8.1, 2.7 Hz), 8.30 (1H, s), 8.26-8.10 (3H, m), 7.75 (1H, br s), 7.68 (1H, t, J = 8.1 Hz), 7.44-7.41 (2H, m), 2.85 (1H, q, J = 8.1 Hz), 1.15 (6H, d, J = 5.4 Hz); LRMS (ESI) m/z 424 [M + H]$^+$. |
| 3 | 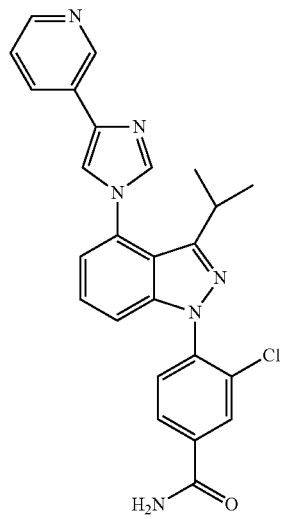 [SMILES: CC(C)c1nn(-c2ccc(C(N)=O)cc2Cl)c2cccc(-n3cnc(-c4cccnc4)c3)c12] | $^1$H-NMR (DMSO-$d_6$): δ 9.07 (1H, s), 8.42 (1H, d, J = 5.4 Hz), 8.30 (1H, s), 8.24-8.16 (3H, m), 8.02 (1H, dd, J = 8.1, 2.7 Hz), 7.70-7.68 (2H, m), 7.54 (1H, dd, J = 8.1, 5.4 Hz), 7.42-7.38 (2H, m), 7.30 (1H, d, J = 5.4 Hz), 2.84 (1H, q, J = 8.1 Hz), 1.08 (6H, d, J = 6.8 Hz); LRMS (ESI) m/z 457 [M + H]$^+$. |

TABLE 2

| Compound No. | Structural formula | Physical properties |
|---|---|---|
| 4 | | $^1$H-NMR (DMSO-d$_6$): δ 9.10 (1H, d, J = 1.8 Hz), 8.46 (1H, dd, J = 5.4, 1.8 Hz), 8.33 (1H, d, J = 1.8 Hz), 8.23-8.18 (2H, m), 8.01 (1H, s), 7.91 (1H, dd, J = 8.1, 1.8 Hz), 7.52-7.47 (5H, m), 7.31 (1H, d, J = 5.4 Hz), 2.87 (1H, q, J = 8.1 Hz), 2.13 (3H, s), 1.12 (6H, d, J = 5.4 Hz); LRMS (ESI) m/z 437 [M + H]$^+$. |
| 5 | | $^1$H-NMR (DMSO-d$_6$): δ 8.27 (1H, br s), 8.24 (1H, d, J = 2.7 Hz), 8.06-8.03 (2H, m), 7.94 (1H, s), 7.75-7.71 (3H, m), 7.54 (1H, t, J = 8.1 Hz), 7.39 (1H, d, J = 8.1 Hz), 7.27 (1H, d, J = 8.1 Hz), 3.86 (3H, s), 2.88 (1H, q, J = 8.1 Hz), 1.11 (6H, d, J = 6.8 Hz); LRMS (ESI) m/z 460 [M + H]$^+$. |
| 6 | | $^1$H-NMR (DMSO-d$_6$): δ 8.12 (1H, br s), 8.02 (2H, m), 7.94 (1H, s), 7.91 (1H, dd, J = 8.1, 2.7 Hz), 7.73 (2H, d, J = 10.8 Hz), 7.54-7.48 (3H, m), 7.38 (1H, d, J = 8.1 Hz), 7.24 (1H, d, J = 8.1 Hz), 3.86 (3H, s), 2.88 (1H, q, J = 8.1 Hz), 2.50-2.45 (2H, m), 1.11 (6H, d, J = 5.4 Hz), 1.00 (3H, t, J = 8.1 Hz); LRMS (ESI) m/z 454 [M + H]$^+$. |

TABLE 3

| Compound No. | Structural formula | Physical properties |
|---|---|---|
| 7 | | $^1$H-NMR (DMSO-$d_6$): δ 9.07 (1H, d, J = 2.1 Hz), 8.40 (1H, dd, J = 8.4, 2.1 Hz), 8.24 (1H, d, J = 8.4 Hz), 8.15 (1H, s), 8.08 (1H, d, J = 8.4 Hz), 8.01 (1H, s), 7.95 (1H, s), 7.72 (3H, s), 7.65 (1H, t, J = 8.1 Hz), 7.34 (1H, d, J = 8.1 Hz), 3.86 (3H, s), 2.85 (1H, q, J = 8.1 Hz), 1.14 (6H, d, J = 5.4 Hz); LRMS (ESI) m/z 427 [M + H]$^+$. |
| 8 | | $^1$H-NMR (DMSO-$d_6$): δ 8.09 (1H, br s), 8.01 (2H, m), 7.94 (1H, s), 7.90 (1H, d, J = 8.1 Hz), 7.73 (2H, d, J = 10.8 Hz), 7.53-7.50 (3H, m), 7.39 (1H, d, J = 10.8 Hz), 7.25 (1H, d, J = 8.1 Hz), 3.86 (3H, s), 2.87 (1H, q, J = 8.1 Hz), 2.15 (3H, s), 1.11 (6H, d, J = 6.8 Hz); LRMS (ESI) m/z 440 [M + H]$^+$. |
| 9 | | $^1$H-NMR (DMSO-$d_6$): δ 8.68 (1H, s), 7.95 (4H, m), 7.80 (1H, d, J = 8.1 Hz), 7.71 (2H, s), 7.61 (1H, t, J = 8.1 Hz), 7.27 (1H, d, J = 8.1 Hz), 7.16 (1H, d, J = 2.7 Hz), 6.89 (1H, dd, J = 8.1, 1.8 Hz), 3.86 (3H, s), 2.83 (1H, q, J = 8.1 Hz), 1.39 (9H, s), 1.12 (6H, d, J = 5.4 Hz); LRMS (ESI) m/z 497 [M + H]$^+$. |

TABLE 4

| Compound No. | Structural formula | Physical properties |
| --- | --- | --- |
| 10 | | $^1$H-NMR (DMSO-d$_6$): δ 9.10 (1H, s), 8.46 (1H, d, J = 5.4 Hz), 8.31 (1H, s), 8.23-8.19 (2H, m), 8.03 (1H, s), 7.58-7.55 (2H, m), 7.46-7.27 (5H, m), 5.21 (1H, d, J = 8.1 Hz), 3.74 (1H, q, J = 5.4 Hz), 2.84 (1H, q, J = 5.4 Hz), 1.13 (12H, dd, J = 8.1, 5.4 Hz); LRMS (ESI) m/z 480 [M + H]$^+$. |
| 11 | | $^1$H-NMR (DMSO-d$_6$): δ 9.10 (1H, d, J = 2.7 Hz), 8.46 (1H, d, J = 2.7 Hz), 8.30 (1H, d, J = 2.7 Hz), 8.23-8.19 (2H, m), 7.57 (2H, d, J = 2.7 Hz), 7.46-7.38 (3H, m), 7.33-7.30 (3H, m), 5.60 (1H, d, J = 8.1 Hz), 4.03-4.00 (1H, m), 2.86 (1H, q, J = 5.4 Hz), 2.40-2.36 (2H, m), 1.74-1.70 (4H, m), 1.15 (7H, d, J = 6.8 Hz); LRMS (ESI) m/z 492 [M + H]$^+$. |
| 12 | | $^1$H-NMR (DMSO-d$_6$): δ 8.00 (1H, d, J = 1.8 Hz), 7.94 (1H, s), 7.72-7.72 (2H, m), 7.55-7.54 (2H, m), 7.40-7.39 (3H, m), 7.28-7.26 (2H, m), 5.21 (1H, d, J = 8.1 Hz), 3.86 (3H, s), 3.81-3.68 (1H, m), 2.85 (1H, q, J = 5.4 Hz), 1.12 (12H, dd, J = 8.1, 2.7 Hz); LRMS (ESI) m/z 483 [M + H]$^+$. |

TABLE 5

| Compound No. | Structural formula | Physical properties |
|---|---|---|
| 13 | | $^1$H-NMR (DMSO-d$_6$): δ 8.01 (1H, br s), 7.99 (1H, d, J = 2.7 Hz), 7.95 (1H, s), 7.72 (2H, s), 7.59-7.37 (3H, m), 7.32-7.25 (2H, m), 5.60 (1H, d, J = 8.1 Hz), 4.01-3.98 (1H, m), 3.86 (3H, s), 2.85 (1H, q, J = 5.4 Hz), 2.39-2.36 (2H, m), 1.72 (4H, br s), 1.13 (6H, d, J = 5.4 Hz); LRMS (ESI) m/z 495 [M + H]$^+$. |
| 14 | | $^1$H-NMR (DMSO-d$_6$): δ 8.72 (1H, s), 7.99 (1H, d, J = 5.4 Hz), 7.94 (1H, s), 7.89 (1H, s), 7.86 (1H, d, J = 5.4 Hz), 7.78 (1H, t, J = 5.4 Hz), 7.70 (1H, s), 7.60 (1H, s), 7.52 (1H, d, J = 5.4 Hz), 7.14 (1H, d, J = 2.7 Hz), 6.91 (1H, dd, J = 5.4, 1.8 Hz), 3.87 (3H, s), 1.39 (9H, s); LRMS (ESI) m/z 523 [M + H]$^+$. |
| 15 | | $^1$H-NMR (DMSO-d$_6$): δ 8.44 (1H, t, J = 2.7 Hz), 8.13 (1H, d, J = 8.1 Hz), 8.00 (1H, s), 7.95-7.94 (2H, m), 7.83 (1H, t, J = 5.4 Hz), 7.76 (1H, s), 7.67 (1H, s), 7.58 (1H, d, J = 5.4 Hz), 7.03 (1H, d, J = 1.8 Hz), 6.98 (1H, dd, J = 5.4, 1.8 Hz), 3.93 (3H, s), 3.27 (2H, q, J = 5.4 Hz), 1.30 (3H, t, J = 5.4 Hz); LRMS (ESI) m/z 495 [M + H]$^+$. |

TABLE 6

| Compound No. | Structural formula | Physical properties |
|---|---|---|
| 16 | (pyridin-3-yl-imidazole linked to 4-position of 3-CF₃-indazole; N1 bears 4-(tert-butylamino)benzamide) | ¹H-NMR (DMSO-d₆): δ 9.14 (1H, s), 8.78 (1H, s), 8.53 (1H, d, J = 2.7 Hz), 8.26-8.25 (2H, m), 8.14 (1H, s), 8.09 (1H, d, J = 5.4 Hz), 7.93 (1H, d, J = 5.4 Hz), 7.88 (1H, t, J = 5.4 Hz), 7.65 (1H, d, J = 5.4 Hz), 7.50 (1H, dd, J = 5.4, 2.7 Hz), 7.20 (1H, d, J = 1.8 Hz), 6.98 (1H, dd, J = 5.4, 1.8 Hz), 1.45 (9H, s); LRMS (ESI) m/z 520 [M + H]⁺. |
| 17 | (pyridin-3-yl-imidazole linked to 4-position of 3-CF₃-indazole; N1 bears 2-methyl-4-carbamoylphenyl) | ¹H-NMR (DMSO-d₆): δ 8.23-8.20 (3H, m), 8.11 (2H, d, J = 5.4 Hz), 7.99 (1H, dd, J = 5.4, 2.7 Hz), 7.76 (1H, t, J = 5.4 Hz), 7.67 (1H, d, J = 5.4 Hz), 7.62-7.59 (3H, m), 2.13 (3H, s); LRMS (ESI) m/z 463 [M + H]⁺. |
| 18 | (1-methylpyrazol-4-yl-imidazole linked to 4-position of 3-CF₃-indazole; N1 bears 2-ethyl-4-carbamoylphenyl) | ¹H-NMR (DMSO-d₆): δ 8.20 (1H, s), 8.10 (1H, d, J = 1.8 Hz), 7.97 (1H, dd, J = 5.4, 1.8 Hz), 7.93 (2H, s), 7.73-7.64 (4H, m), 7.56 (1H, d, J = 5.4 Hz), 7.52 (1H, d, J = 5.4 Hz), 3.87 (3H, s), 2.40 (2H, q, J = 5.4 Hz), 1.03 (3H, t, J = 5.4 Hz); LRMS (ESI) m/z 480 [M + H]⁺. |

TABLE 7

| Compound No. | Structural formula | Physical properties |
|---|---|---|
| 19 | (structure) | $^1$H-NMR (DMSO-d$_6$): δ 9.09 (1H, s), 8.47 (1H, s), 8.24-8.20 (2H, m), 8.12-8.11 (2H, m), 7.98 (1H, dd, J = 5.4, 1.8 Hz), 7.75 (1H, t, J = 5.4 Hz), 7.66 (1H, d, J = 5.4 Hz), 7.61-7.59 (2H, m), 7.45 (1H, dd, J = 5.4, 1.8 Hz), 2.40 (2H, q, J = 5.4 Hz), 1.04 (3H, t, J = 5.4 Hz); LRMS (ESI) m/z 477 [M + H]$^+$. |
| 20 | (structure) | $^1$H-NMR (DMSO-d$_6$): δ 8.07 (1H, s), 7.94 (1H, s), 7.89 (1H, s), 7.71 (1H, s), 7.68 (1H, t, J = 5.4 Hz), 7.59 (1H, s), 7.51-7.43 (4H, m), 7.29 (1H, d, J = 5.4 Hz), 7.23 (1H, dd, J = 5.4, 1.8 Hz), 5.04 (1H, d, J = 5.4 Hz), 3.87 (3H, s), 3.78 (1H, q, J = 5.4 Hz), 1.10 (6H, d, J = 2.7 Hz); LRMS (ESI) m/z 509 [M + H]$^+$. |
| 21 | (structure) | $^1$H-NMR (DMSO-d$_6$): δ 8.06 (1H, s), 7.95 (1H, s), 7.88 (1H, s), 7.71 (1H, s), 7.68 (1H, t, J = 5.4 Hz), 7.58 (1H, s), 7.48-7.46 (2H, m), 7.30-7.28 (2H, m), 7.25 (1H, dd, J = 5.4, 1.8 Hz), 5.62 (1H, d, J = 5.4 Hz), 4.01 (1H, q, J = 5.4 Hz), 3.87 (3H, s), 2.34-2.30 (2H, m), 1.83-1.77 (2H, m), 1.70-1.66 (2H, m); LRMS (ESI) m/z 521 [M + H]$^+$. |

TABLE 8

| Compound No. | Structural formula | Physical properties |
|---|---|---|
| 22 | | $^1$H-NMR (DMSO-d$_6$): δ 9.09 (1H, d, J = 2.7 Hz), 8.47 (1H, dd, J = 2.7, 1.8 Hz), 8.22 (1H, dt, J = 5.4, 1.8 Hz), 8.15 (1H, s), 8.08 (1H, s), 8.05 (1H, s), 7.71 (1H, t, J = 5.4 Hz), 7.54 (2H, dd, J = 5.4, 2.7 Hz), 7.46-7.44 (2H, m), 7.30 (1H, d, J = 5.4 Hz), 7.24 (1H, dd, J = 5.4, 2.7 Hz), 5.06 (1H, d, J = 5.4 Hz), 3.77 (1H, q, J = 5.4 Hz), 1.10 (6H, d, J = 5.4 Hz); LRMS (ESI) m/z 506 [M + H]$^+$. |
| 23 | | $^1$H-NMR (DMSO-d$_6$): δ 9.10 (1H, d, J = 2.7 Hz), 8.48 (1H, dd, J = 2.7, 1.8 Hz), 8.22 (1H, d, J = 5.4 Hz), 8.14 (1H, s), 8.06-8.04 (2H, m), 7.71 (1H, t, J = 5.4 Hz), 7.53 (2H, dd, J = 8.1, 2.7 Hz), 7.46-7.44 (2H, m), 7.30 (2H, d, J = 5.4 Hz), 5.64 (1H, d, J = 2.7 Hz), 4.02 (1H, q, J = 5.4 Hz), 2.32-2.31 (2H, m), 1.83-1.78 (2H, m), 1.70-1.66 (2H, m); LRMS (ESI) m/z 518 [M + H]$^+$. |
| 24 | | $^1$H-NMR (DMSO-d$_6$): δ 7.94 (1H, s), 7.84 (1H, s), 7.71 (1H, s), 7.68 (1H, t, J = 5.4 Hz), 7.57 (1H, s), 7.49-7.47 (3H, m), 7.30 (1H, d, J = 5.4 Hz), 7.18 (1H, dd, J = 5.4, 1.8 Hz), 5.43 (2H, br s), 3.87 (3H, s); LRMS (ESI) m/z 467 [M + H]$^+$. |

TABLE 9

| Compound No. | Structural formula | Physical properties |
|---|---|---|
| 25 | | $^1$H-NMR (DMSO-d$_6$): δ 9.09 (1H, d, J = 1.8 Hz), 8.47 (1H, dd, J = 5.4, 1.8 Hz), 8.21 (1H, dt, J = 5.4, 1.8 Hz), 8.13 (1H, s), 8.03 (1H, s), 7.71 (1H, t, J = 5.4 Hz), 7.54-7.53 (2H, m), 7.47-7.43 (2H, m), 7.31 (1H, d, J = 5.4 Hz), 7.19 (1H, dd, J = 5.4, 2.7 Hz), 5.45 (2H, s); LRMS (ESI) m/z 464 [M + H]$^+$. |
| 26 | | $^1$H-NMR (DMSO-D$_6$) δ: 8.16 (1H, d, J = 1.5 Hz), 8.11 (1H, s), 8.02 (1H, d, J = 1.7 Hz), 7.98 (1H, s), 7.90 (1H, dd, J = 8.0, 1.7 Hz), 7.88 (1H, d, J = 1.5 Hz), 7.77 (1H, s), 7.70 (1H, d, J = 3.4 Hz), 7.52 (1H, s), 7.48 (1H, d, J = 8.0 Hz), 7.29 (1H, d, J = 0.5 Hz), 7.28 (1H, d, J = 0.5 Hz), 7.06 (1H, dd, J = 3.4, 3.4 Hz), 6.85 (1H, d, J = 3.4 Hz), 3.88 (3H, s), 2.09 (3H, s).; LRMS (ESI) m/z 397 [M + H]$^+$. |
| 27 | | $^1$H-NMR (DMSO-D$_6$) δ: 8.17 (1H, d, J = 1.5 Hz), 8.15 (1H, s), 8.04 (1H, d, J = 2.0 Hz), 7.99 (1H, s), 7.91 (1H, dd, J = 8.0, 2.0 Hz), 7.89 (1H, d, J = 1.5 Hz), 7.77 (1H, s), 7.68 (1H, d, J = 3.4 Hz), 7.54 (1H, s), 7.45 (1H, d, J = 8.0 Hz), 7.28 (1H, s), 7.27 (1H, d, J = 2.2 Hz), 7.02 (1H, ddd, J = 0.7, 3.4, 5.6 Hz), 6.85 (1H, dd, J = 3.4, 0.7 Hz), 3.88 (3H, s), 2.42-2.33 (2H, m), 0.99 (3H, t, J = 7.6 Hz).; LRMS (ESI) m/z 411 [M + H]$^+$. |

TABLE 10

| Compound No. | Structural formula | Physical properties |
|---|---|---|
| 25 | | $^1$H-NMR (DMSO-d$_6$): δ 9.09 (1H, d, J = 1.8 Hz), 8.47 (1H, dd, J = 5.4, 1.8 Hz), 8.21 (1H, dt, J = 5.4, 1.8 Hz), 8.13 (1H, s), 8.03 (1H, s), 7.71 (1H, t, J = 5.4 Hz), 7.54-7.53 (2H, m), 7.47-7.43 (2H, m), 7.31 (1H, d, J = 5.4 Hz), 7.19 (1H, dd, J = 5.4, 2.7 Hz), 5.45 (2H, s); LRMS (ESI) m/z 464 [M + H]$^+$. |
| 26 | | $^1$H-NMR (DMSO-D$_6$) δ: 8.16 (1H, d, J = 1.5 Hz), 8.11 (1H, s), 8.02 (1H, d, J = 1.7 Hz), 7.98 (1H, s), 7.90 (1H, dd, J = 8.0, 1.7 Hz), 7.88 (1H, d, J = 1.5 Hz), 7.77 (1H, s), 7.70 (1H, d, J = 3.4 Hz), 7.52 (1H, s), 7.48 (1H, d, J = 8.0 Hz), 7.29 (1H, d, J = 0.5 Hz), 7.28 (1H, d, J = 0.5 Hz), 7.06 (1H, dd, J = 3.4, 3.4 Hz), 6.85 (1H, d, J = 3.4 Hz), 3.88 (3H, s), 2.09 (3H, s).; LRMS (ESI) m/z 397 [M + H]$^+$ |
| 27 | | $^1$H-NMR (DMSO-D$_6$) δ: 8.17 (1H, d, J = 1.5 Hz), 8.15 (1H, s), 8.04 (1H, d, J = 2.0 Hz), 7.99 (1H, s), 7.91 (1H, dd, J = 8.0, 2.0 Hz), 7.89 (1H, d, J = 1.5 Hz), 7.77 (1H, s), 7.68 (1H, d, J = 3.4 Hz), 7.54 (1H, s), 7.45 (1H, d, J = 8.0 Hz), 7.28 (1H, s), 7.27 (1H, d, J = 2.2 Hz), 7.02 (1H, ddd, J = 0.7, 3.4, 5.6 Hz), 6.85 (1H, dd, J = 3.4, 0.7 Hz), 3.88 (3H, s), 2.42-2.33 (2H, m), 0.99 (3H, t, J = 7.6 Hz).; LRMS (ESI) m/z 411 [M + H]$^+$ |

TABLE 11

| Compound No. | Structural formula | Physical properties |
|---|---|---|
| 28 | | $^1$H-NMR (DMSO-D$_6$) δ: 8.23 (1H, s), 8.16 (1H, d, J = 1.5 Hz), 8.02 (1H, d, J = 11.7 Hz), 7.99 (1H, s), 7.96 (1H, d, J = 8.3 Hz), 7.87 (1H, d, J = 1.5 Hz), 7.81-7.78 (3H, m), 7.70 (1H, s), 7.34-7.34 (3H, m), 6.91 (1H, d, J = 2.9 Hz), 3.88 (3H, s).; LRMS (ESI) m/z 401 [M + H]$^+$ |
| 29 | | $^1$H-NMR (DMSO-D$_6$) δ: 8.28 (1H, s), 8.25 (1H, d, J = 2.0 Hz), 8.16 (1H, d, J = 1.2 Hz), 8.06 (1H, dd, J = 8.3, 2.0 Hz), 7.99 (1H, s), 7.88 (1H, d, J = 1.2 Hz), 7.77 (1H, s), 7.74 (1H, d, J = 8.3 Hz), 7.73 (1H, d, J = 3.4 Hz), 7.72 (1H, s), 7.32 (1H, d, J = 2.0 Hz), 7.31 (1H, s), 7.13 (1H, ddd, J = 0.5, 4.1, 4.9 Hz), 6.88 (1H, dd, J = 3.4, 0.5 Hz), 3.88 (3H, s).; LRMS (ESI) m/z 417 [M + H]$^+$ |
| 30 | | $^1$H-NMR (DMSO-D$_6$) δ: 8.39 (1H, d, J = 2.0 Hz), 8.28 (1H, s), 8.16 (1H, d, J = 1.5 Hz), 8.09 (1H, dd, J = 8.0, 2.0 Hz), 7.99 (1H, s), 7.88 (1H, d, J = 1.5 Hz), 7.77 (1H, s), 7.71 (1H, d, J = 3.4 Hz), 7.71 (1H, d, J = 8.0 Hz), 7.71 (1H, s), 7.31 (1H, s), 7.30 (1H, d, J = 1.0 Hz), 7.09 (1H, ddd, J = 0.7, 4.6, 4.6 Hz), 6.87 (1H, dd, J = 3.4, 0.7 Hz), 3.88 (3H, s).; LRMS (ESI) m/z 462 [M + H]$^+$ |

TABLE 12

| Compound No. | Structural formula | Physical properties |
|---|---|---|
| 31 | | ¹H-NMR (DMSO-D₆) δ: 8.14 (1H, d, J = 1.5 Hz), 7.99 (1H, s), 7.93 (1H, s), 7.85 (1H, d, J = 1.5 Hz), 7.77 (1H, s), 7.58 (1H, d, J = 3.4 Hz), 7.44 (1H, d, J = 0.7 Hz), 7.34 (1H, s), 7.28 (1H, d, J = 2.7 Hz), 7.27 (1H, s), 7.17 (1H, d, J = 2.7 Hz), 7.17 (1H, s), 7.08 (1H, ddd, J = 3.4, 5.9, 0.7 Hz), 6.85 (1H, dd, J = 3.4, 0.7 Hz), 5.06 (2H, s), 3.88 (3H, s).; LRMS (ESI) m/z 398 [M + H]⁺ |
| 32 | | ¹H-NMR (DMSO-D₆) δ: 8.14 (1H, d, J = 1.5 Hz), 8.04 (1H, s), 7.99 (1H, s), 7.85 (1H, d, J = 1.5 Hz), 7.77 (1H, d, J = 0.5 Hz), 7.58 (1H, d, J = 3.4 Hz), 7.41 (1H, s), 7.35 (1H, d, J = 1.8 Hz), 7.28 (1H, s), 7.27 (1H, s), 7.23 (1H, dd, J = 7.8, 1.8 Hz), 7.18 (1H, d, J = 1.8 Hz), 7.06-7.02 (1H, m), 6.86 (1H, dd, J = 3.4, 0.7 Hz), 4.70 (1H, t, J = 5.7 Hz), 3.88 (3H, s), 3.15 (2H, dq, J = 5.7, 7.0 Hz), 1.06 (3H, t, J = 7.0 Hz). |
| 33 | | ¹H-NMR (DMSO-D₆) δ: 8.16 (1H, d, J = 1.2 Hz), 8.04 (1H, s), 7.99 (1H, s), 7.87 (1H, d, J = 1.2 Hz), 7.77 (1H, d, J = 0.7 Hz), 7.59 (1H, d, J = 3.4 Hz), 7.42 (1H, s), 7.40 (1H, d, J = 1.7 Hz), 7.29 (1H, d, J = 0.7 Hz), 7.28 (1H, s), 7.24 (1H, dd, J = 8.0, 1.7 Hz), 7.19 (1H, d, J = 8.0 Hz), 7.08-7.04 (1H, m), 6.88 (1H, dd, J = 3.4, 0.7 Hz), 4.12 (1H, d, J = 8.5 Hz), 3.87 (3H, d, J = 4.4 Hz), 3.75-3.67 (1H, m), 1.05 (6H, d, J = 6.3 Hz).; LRMS (ESI) m/z 440 [M + H]⁺ |

TABLE 13

| Compound No. | Structural formula | Physical properties |
|---|---|---|
| 34 | | $^1$H-NMR (DMSO-D$_6$) δ: 8.39 (1H, t, J = 5.1 Hz), 8.14 (1H, d, J = 1.5 Hz), 7.99 (1H, s), 7.96 (1H, s), 7.86 (1H, d, J = 3.4 Hz), 7.84 (1H, d, J = 1.5 Hz), 7.83 (1H, d, J = 7.1 Hz), 7.77 (1H, d, J = 0.5 Hz), 7.70 (1H, d, J = 8.0 Hz), 7.35 (1H, t, J = 7.9 Hz), 7.30 (1H, dd, J = 1.9, 0.7 Hz), 7.27 (1H, s), 6.84 (1H, d, J = 3.4 Hz), 6.79 (1H, d, J = 2.0 Hz), 6.76 (1H, dd, J = 8.3, 2.0 Hz), 3.88 (3H, s), 3.21 (2H, dt, J = 5.1, 7.2 Hz), 1.23 (3H, t, J = 7.2 Hz).; LRMS (ESI) m/z 426 [M + H]$^+$ |
| 35 | | $^1$H-NMR (DMSO-D$_6$) δ: 8.74 (1H, s), 8.14 (1H, d, J = 1.2 Hz), 7.98 (1H, s), 7.95 (1H, brs), 7.84 (1H, d, J = 1.2 Hz), 7.81 (1H, d, J = 8.0 Hz), 7.81 (1H, d, J = 3.4 Hz), 7.76 (1H, d, J = 0.7 Hz), 7.61 (1H, d, J = 8.3 Hz), 7.37 (1H, dd, J = 8.0, 8.0 Hz), 7.30 (1H, d, J = 8.0 Hz), 7.26 (1H, s), 6.90 (1H, d, J = 2.0 Hz), 6.84 (1H, d, J = 3.4 Hz), 6.73 (1H, dd, J = 8.3, 2.0 Hz), 3.88 (3H, s), 1.39 (9H, s).; LRMS (ESI) m/z 454 [M + H]$^+$ |
| 36 | | $^1$H-NMR (DMSO-D$_6$) δ: 9.15 (1H, s), 8.45 (1H, s), 8.40 (1H, s), 8.32 (1H, s), 8.26 (1H, s), 8.12 (1H, s), 8.01 (1H, s), 7.89 (1H, s), 7.71 (1H, s), 7.52-7.46 (3H, m), 7.33 (2H, s), 7.09 (1H, s), 6.88 (1H, s), 2.49 (3H, s).; LRMS (ESI) m/z 394 [M + H]$^+$ |

TABLE 14

| Compound No. | Structural formula | Physical properties |
|---|---|---|
| 37 | | $^1$H-NMR (DMSO-D$_6$) δ: 9.15 (1H, s), 8.45 (1H, s), 8.41 (1H, s), 8.32 (1H, s), 8.26 (1H, d, J = 7.6 Hz), 8.15 (1H, s), 8.04 (1H, s), 7.91 (1H, d, J = 7.6 Hz), 7.69 (1H, s), 7.53 (1H, s), 7.44 (2H, d, J = 7.6 Hz), 7.34-7.27 (2H, m), 7.05 (1H, d, J = 7.6 Hz), 6.88 (1H, s), 2.43-2.35 (2H, m), 0.98 (3H, t, J = 7.6 Hz).; LRMS (ESI) m/z 408 [M + H]$^+$ |
| 38 | | $^1$H-NMR (DMSO-D$_6$) δ: 9.16 (1H, s), 8.48 (1H, s), 8.41 (1H, d, J = 1.2 Hz), 8.33 (1H, d, J = 1.2 Hz), 8.27 (1H, d, J = 7.8 Hz), 8.25 (1H, d, J = 5.9 Hz), 8.03 (1H, dd, J = 11.5, 1.7 Hz), 7.96 (1H, dd, J = 8.3, 1.7 Hz), 7.83-7.79 (2H, m), 7.71 (1H, s), 7.45 (1H, dd, J = 7.6, 4.9 Hz), 7.39 (3H, s), 6.95 (1H, d, J = 3.4 Hz).; LRMS (ESI) m/z 398 [M + H]$^+$ |
| 39 | | $^1$H-NMR (DMSO-D$_6$) δ: 9.16 (1H, s), 8.47 (1H, s), 8.41 (1H, d, J = 1.2 Hz), 8.33 (1H, d, J = 1.2 Hz), 8.29-8.25 (3H, m), 8.07 (1H, dd, J = 8.3, 2.0 Hz), 7.76 (1H, s), 7.75 (1H, d, J = 4.6 Hz), 7.73 (1H, s), 7.45 (1H, dd, J = 4.6, 7.6 Hz), 7.37 (1H, dt, J = 1.5, 7.6 Hz), 7.34 (1H, t, J = 7.6 Hz), 7.18 (1H, d, J = 7.6 Hz), 6.93 (1H, d, J = 3.4 Hz).; LRMS (ESI) m/z 414 [M + H]$^+$ |

TABLE 15

| Compound No. | Structural formula | Physical properties |
|---|---|---|
| 40 | | ¹H-NMR (DMSO-D₆) δ: 9.16 (1H, d, J = 1.7 Hz), 8.47 (1H, dd, J = 4.8, 1.7 Hz), 8.38 (1H, d, J = 1.2 Hz), 8.30 (1H, d, J = 1.2 Hz), 8.27 (1H, dt, J = 8.0, 2.0 Hz), 7.93 (1H, s), 7.60 (1H, d, J = 3.4 Hz), 7.45 (1H, dt, J = 0.7, 6.7 Hz), 7.45 (1H, s), 7.35-7.29 (3H, m), 7.18 (1H, dt, J = 1.5, 8.3 Hz), 7.18 (1H, s), 7.12 (1H, d, J = 7.6 Hz), 6.89 (1H, dd, J = 0.7, 3.4 Hz), 5.06 (2H, s).; LRMS (ESI) m/z 395 [M + H]⁺ |
| 41 | | ¹H-NMR (DMSO-D₆) δ: 9.16 (1H, d, J = 2.0 Hz), 8.47 (1H, dd, J = 4.8, 1.6 Hz), 8.38 (1H, d, J = 1.2 Hz), 8.31 (1H, d, J = 1.2 Hz), 8.27 (1H, dt, J = 7.9, 2.0 Hz), 8.04 (1H, s), 7.60 (1H, d, J = 3.2 Hz), 7.45 (1H, dd, J = 7.9, 4.8 Hz), 7.41 (1H, s), 7.36 (1H, d, J = 1.2 Hz), 7.34 (1H, dd, J = 7.6, 1.2 Hz), 7.31 (1H, d, J = 7.6 Hz), 7.24 (1H, dd, J = 7.8, 1.6 Hz), 7.18 (1H, d, J = 7.8 Hz), 7.08 (1H, d, J = 7.8 Hz), 6.91 (1H, d, J = 3.2 Hz), 4.71 (1H, t, J = 5.7 Hz), 3.15 (2H, dq, J = 5.7, 7.1 Hz), 1.06 (3H, t, J = 7.1 Hz).; LRMS (ESI) m/z 423 [M + H]⁺ |
| 42 | | ¹H-NMR (DMSO-D₆) δ: 9.16 (1H, s), 8.47 (1H, d, J = 3.7 Hz), 8.40 (1H, s), 8.33 (1H, s), 8.27 (1H, d, J = 7.8 Hz), 8.05 (1H, s), 7.62 (1H, d, J = 3.2 Hz), 7.47-7.41 (3H, m), 7.36-7.30 (2H, m), 7.26 (1H, d, J = 7.8 Hz), 7.20 (1H, d, J = 7.8 Hz), 7.10 (1H, d, J = 7.8 Hz), 6.92 (1H, d, J = 3.2 Hz), 4.13 (1H, d, J = 8.3 Hz), 3.72 (1H, dq, J = 8.3, 6.1 Hz), 1.06 (6H, d, J = 6.1 Hz).; LRMS (ESI) m/z 437 [M + H]⁺ |

TABLE 16

| Compound No. | Structural formula | Physical properties |
| --- | --- | --- |
| 43 | | ¹H-NMR (DMSO-D₆) δ: 9.16 (1H, s), 8.47 (1H, d, J = 4.6 Hz), 8.40 (1H, t, J = 4.6 Hz), 8.38 (1H, d, J = 1.2 Hz), 8.31 (1H, d, J = 1.2 Hz), 8.27 (1H, dt, J = 7.9, 2.0 Hz), 7.98 (1H, s), 7.89 (1H, d, J = 3.4 Hz), 7.85 (1H, d, J = 8.3 Hz), 7.74 (1H, dd, J = 7.3, 1.2 Hz), 7.45 (1H, dd, J = 7.7, 5.0 Hz), 7.38 (1H, q, J = 7.6 Hz), 7.37 (1H, s), 7.29 (1H, s), 6.88 (1H, d, J = 3.4 Hz), 6.80 (1H, d, J = 2.0 Hz), 6.78 (1H, dd, J = 8.3, 2.0 Hz), 3.22 (2 H, dq, J = 5.0, 7.2 Hz), 1.24 (3H, t, J = 7.2 Hz).; LRMS (ESI) m/z 423 [M + H]⁺ |
| 44 | | ¹H-NMR (DMSO-D₆) δ: 9.15 (1H, d, J = 1.7 Hz), 8.75 (1H, s), 8.47 (1H, dd, J = 4.9, 1.5 Hz), 8.39 (1H, d, J = 1.2 Hz), 8.31 (1H, d, J = 1.2 Hz), 8.27 (1H, dt, J = 7.9, 2.0 Hz), 7.97 (1H, s), 7.84 (1H, d, J = 3.4 Hz), 7.83 (1H, d, J = 7.8 Hz), 7.66 (1H, d, J = 7.8 Hz), 7.45 (1H, dd, J = 7.6, 4.9 Hz), 7.41 (1H, t, J = 7.6 Hz), 7.37 (1H, dd, J = 7.6, 1.0 Hz), 7.28 (1H, s), 6.91 (1H, d, J = 2.0 Hz), 6.88 (1H, d, J = 3.4 Hz), 6.74 (1H, dd, J = 8.3, 2.0 Hz), 1.39 (9H, s).; LRMS (ESI) m/z 451 [M + H]⁺ |
| 45 | | ¹H-NMR (DMSO-D₆) δ: 8.11 (1H, s), 8.02 (1H, d, J = 1.7 Hz), 7.92 (1H, s), 7.89 (1H, s), 7.87 (1 H, dd, J = 7.8, 2.0 Hz), 7.71 (1H, s), 7.63 (1H, d, J = 1.2 Hz), 7.49 (1H, s), 7.38 (2H, dd, J = 3.2, 4.4 Hz), 7.21 (1H, t, J = 7.8 Hz), 7.10 (1H, d, J = 7.3 Hz), 7.04 (1H, d, J = 8.3 Hz), 3.85 (3H, s), 2.43-2.35 (2H, m), 1.88 (3H, s), 1.00 (3H, t, J = 7.6 Hz).; LRMS (ESI) m/z 425 [M + H]⁺ |

TABLE 17
| Compound No. | Structural formula | Physical properties |
|---|---|---|
| 46 | 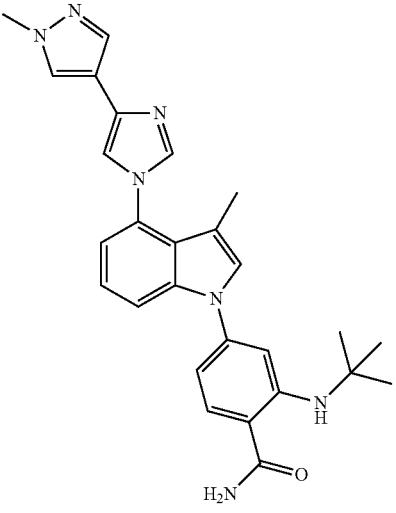 [SMILES: Cc1cn(-c2ccc(C(N)=O)c(NC(C)(C)C)c2)c2cccc(-n3cnc(-c4cnn(C)c4)c3)c12] | $^1$H-NMR (DMSO-D$_6$) δ: 8.74 (1H, s), 7.93 (1H, s), 7.92 (1H, s), 7.87 (1H, d, J = 1.5 Hz), 7.79 (1H, d, J = 8.4 Hz), 7.71 (1H, s), 7.67 (1H, d, J = 8.4 Hz), 7.59 (1H, d, J = 1.1 Hz), 7.54 (1H, d, J = 0.7 Hz), 7.31 (1H, dd, J = 8.4, 7.3 Hz), 7.24 (1H, s), 7.14 (1H, d, J = 7.3 Hz), 6.85 (1H, d, J = 1.8 Hz), 6.68 (1H, dd, J = 8.4, 1.8 Hz), 3.86 (3H, s), 1.86 (3H, s), 1.38 (9H, s).; LRMS (ESI) m/z 468 [M + H]$^+$ |
| 47 | 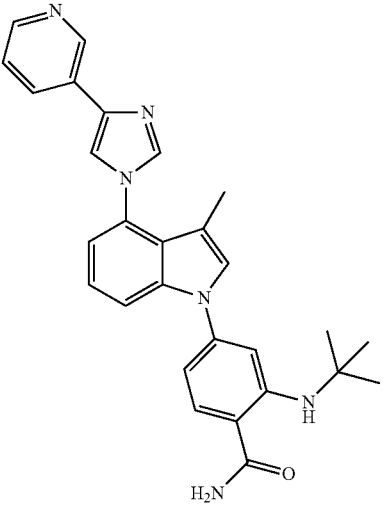 [SMILES: Cc1cn(-c2ccc(C(N)=O)c(NC(C)(C)C)c2)c2cccc(-n3cnc(-c4cccnc4)c3)c12] | $^1$H-NMR (DMSO-D$_6$) δ: 9.10 (1H, d, J = 2.0 Hz), 8.74 (1H, s), 8.45 (1H, dd, J = 4.8, 1.5 Hz), 8.21 (1H, dt, J = 7.9, 1.9 Hz), 8.18 (1H, d, J = 1.1 Hz), 8.06 (1H, d, J = 1.1 Hz), 7.93 (1H, s), 7.79 (1H, d, J = 8.4 Hz), 7.70 (1H, d, J = 8.4 Hz), 7.58 (1H, s), 7.42 (1H, dd, J = 7.9, 4.9 Hz), 7.34 (1H, t, J = 7.9 Hz), 7.24 (1H, s), 7.20 (1H, d, J = 7.3 Hz), 6.86 (1H, d, J = 1.8 Hz), 6.69 (1H, dd, J = 8.2, 2.0 Hz), 1.88 (3H, s), 1.38 (9H, s).; LRMS (ESI) m/z 465 [M + H]$^+$ |

TABLE 18

| Compound No. | Structural formula | Physical properties |
|---|---|---|
| 48 | | $^1$H-NMR (DMSO-D$_6$) δ: 7.92 (1H, s), 7.85 (1H, s), 7.89 (1H, brs), 7.79 (1H, d, J = 8.3 Hz), 7.70 (1H, s), 7.66 (1H, d, J = 8.5 Hz), 7.58 (1H, s), 7.50 (1H, s), 7.31 (1H, t, J = 7.9 Hz), 7.20 (1H, s), 7.12 (1H, d, J = 7.3 Hz), 6.87 (1H, d, J = 1.7 Hz), 6.68 (1H, dd, J = 8.3, 1.7 Hz). |
| 49 | | $^1$H-NMR (DMSO-D$_6$) δ: 8.12 (1H, s), 8.02 (1H, s), 7.92 (1H, s), 7.88 (1H, dd, J = 1.7, 8.0 Hz), 7.88 (1H, s), 7.70 (1H, s), 7.64 (1H, s), 7.50 (1H, s), 7.40 (1H, d, J = 8.0 Hz), 7.39 (1H, s), 7.21 (1H, dd, J = 7.3, 8.3 Hz), 7.09 (1H, d, J = 7.3 Hz), 7.04 (1H, d, J = 8.3 Hz), 3.85 (3H, s), 2.43-2.33 (2H, m), 2.29 (2H, t, J = 7.6 Hz), 1.27-1.20 (2H, m), 0.98 (3H, t, J = 7.6 Hz), 0.66 (3H, t, J = 7.2 Hz).; LRMS (ESI) m/z 453 [M + H]$^+$ |
| 50 | | $^1$H-NMR (CDCl$_3$) δ: 8.36 (1H, s), 7.78 (2H, d, J = 2.0 Hz), 7.72 (1H, d, J = 1.8 Hz), 7.71 (1H, dd, J = 8.4, 0.7 Hz), 7.55 (1H, d, J = 8.4 Hz), 7.28 (1H, dd, J = 7.3, 8.4 Hz), 7.20 (1H, s), 7.12 (1H, dd, J = 7.3, 0.7 Hz), 7.00 (1H, d, J = 1.8 Hz), 6.64 (1H, dd, J = 8.4, 2.0 Hz), 3.98 (3H, s), 2.32 (2H, t, J = 7.7 Hz), 1.48 (9H, s), 1.44-1.36 (2H, m), 0.81 (3H, t, J = 7.3 Hz).; LRMS (ESI) m/z 496 [M + H]$^+$ |

TABLE 19

| Compound No. | Structural formula | Physical properties |
| --- | --- | --- |
| 51 | | ¹H-NMR (DMSO-D₆) δ: 8.12 (1H, s), 8.02 (1H, d, J = 1.7 Hz), 7.92 (1H, s), 7.91 (1H, d, J = 1.2 Hz), 7.89 (1H, dd, J = 2.2, 8.0 Hz), 7.70 (1H, s), 7.66 (1H, d, J = 1.0 Hz), 7.50 (1H, s), 7.42 (1H, d, J = 2.9 Hz), 7.40 (1H, d, J = 5.1 Hz), 7.21 (1 H, dd, J = 7.3, 8.3 Hz), 7.07 (1H, d, J = 7.3 Hz), 7.05 (1H, d, J = 8.3 Hz), 3.85 (3H, s), 2.62 (1H, tt, J = 7.6, 7.6 Hz), 2.41-2.32 (2H, m), 2.41 (3H, t, J = 7.6 Hz), 0.99 (6H, d, J = 7.6 Hz). |
| 52 | | ¹H-NMR (DMSO-D₆) δ: 8.74 (1H, s), 7.93 (2H, s), 7.88 (1H, d, J = 1.2 Hz), 7.79 (1H, d, J = 8.4 Hz), 7.70 (1H, s), 7.66 (1H, d, J = 8.3 Hz), 7.61 (1H, d, J = 1.2 Hz), 7.52 (1H, s), 7.30 (1H, dd, J = 8.3, 7.6 Hz), 7.23 (1H, s), 7.10 (1H, d, J = 7.6 Hz), 6.87 (1H, d, J = 2.0 Hz), 6.68 (1H, dd, J = 8.4, 2.0 Hz), 3.85 (3H, s), 2.56 (1H, tt, J = 6.8, 6.8 Hz), 1.37 (9H, s), 1.03 (6H, d, J = 6.8 Hz).; LRMS (ESI) m/z 496 [M + H]⁺ |

Test Example 1

Measurement of HSP90-binding Activity

First, a solution of purified HSP90 was prepared as follows. A plasmid, pET-HSP90N, expressing an HSP90 N-terminal protein having a His tag at the N-terminal was constructed by inserting a human HSP90 alpha gene (NCBI Reference Sequences Register No. NM_005348) region, which encodes amino acids corresponding to from the 2nd amino acid to the 236th amino acid of human HSP90 alpha protein (NCBI Reference Sequences Register No. NP_005339, full length:732 amino acids), into pET-19b (Novagen Inc). The pET-HSP90N was introduced into *Escherichia coli* cells (BL21 (DE3), Stratagene Inc.), and then the *Escherichia coli* cells were cultured in the presence of 0.5 mM isopropyl-beta-D-thiogalactopyranoside (Sigma-Aldrich Corp.) at 37° C. for 4 hours. The *Escherichia coli* cells were collected, suspended in a lysis buffer (50 mM Tris-HCl (pH 7.5), 200 mM NaCl), and sonicated. The sonicated cell solution was centrifuged (40,000×g, 20 minutes) to obtain supernatant as a crude extract. The crude extract was fractionated by Ni Sepharose High Performance (GE Healthcare Japan Corporation) chromatography and HiLoad 26/60 Superdex 75 pg (GE Healthcare Japan Corporation), and the fraction in which HSP90 protein was concentrated was prepared so as to be a 50 mM Tris-HCl (pH 7.5)/20% glycerol solution as a purified HSP90 solution. The purified HSP90 solution was divided and stored at −80° C. until use.

The HSP90-binding activity was measured by an AlphaScreen competitive assay system. The purified HSP90 solution was diluted with a binding buffer (50 mM Tris-HCl (pH 7.5), 150 mM NaCl, 0.1% Triton-X100, 1 mM DTT, 0.1% BSA) and added to a 384-well plate (No. 3673, Corning Incorporated) containing test substances. After reaction at room temperature for 2 hours, biotin-labeled geldanamycin was added to each reaction solution in an amount of 40 nM, followed by reaction for further 1 hour. Detection mix (20 mM HEPES-KOH (pH 7.5), 0.5% BSA, 0.04 mg/mL Nickel Chelate Acceptor beads, 0.04 mg/mL Streptavidin-coated Donor beads) (No. 6760619C, Perkin Elmer, Inc.) was added to each well in the same amount as that of the reaction solution. After reaction in a dark place at room temperature for 1 hour, the fluorescence intensity in each well was measured with a multilabel plate reader, EnVision (Perkin Elmer, Inc.). The inhibition rate (%) of biotin-labeled geldanamycin binding by a compound of the present invention was determined by the following equation using the fluorescence signal of a test substance-free group (control) as a control. Each compound was added thereto, and the concentration ($IC_{50}$ (μM)) of a compound to inhibit the binding of biotin-labeled geldanamycin to 50% of that of the control was determined as a relative index of HSP90 binding.

Inhibition rate (%)=(C−T)/C×100

T: signal in a well to which a test substance was added
C: signal in a well to which no test substance was added As a result, the compounds of the present invention showed highly satisfactory HSP90-binding activities whereas none of comparative compounds showed HSP90-binding activity (Tables 1 to 9).

Test Example 2

Measurement of Cell Growth Inhibition

Cell growth was measured by a crystal violet staining method. SK-BR-3 cells (HTB-30) purchased from American Type Culture Collection were seeded in a 96-well plate (No. 353075, BD Biosciences) at a concentration of 5000 cells/well. The cells were cultured in a 5% $CO_2$ incubator at 37° C. for 24 hours, and then test substances were added to the plate, followed by culturing for further 72 hours. A 25% glutaraldehyde solution (No. 17025-25, Nacalai Tesque Inc.) was added to each well in an amount of 20 μL for 200 μL of the culture medium, and the plate was left to stand at room temperature for 20 minutes for fixing the cells. The plate was washed with water and dried, and then 100 μL of a solution of 0.05% crystal violet (No. 038-17792, Wako Pure Chemical Industries, Ltd.) in 20% methanol was added to each well. The plate was left to stand at room temperature for 20 minutes for staining the cells. The plate was washed with water and dried, and 100 μL of a mixed solution of 0.05 M $NaH_2PO_4$ and ethanol (mixture in equal amounts) was added to each well. The absorbance at 540 nm was measured with a microplate reader (MTP-450, Corona Electric Co., Ltd.) as an index of the number of cells in each well. The inhibition rate (%) of cell growth by a compound of the present invention was determined by the following equation using the absorbance of a drug-untreated group (control) as a control. Each compound was added thereto, and the concentration ($IC_{50}$ (μM)) of a compound to inhibit the number of cells to 50% of that of the control was determined.

Inhibition rate (%)=(C−T)/C×100

T: absorbance in a well to which a test substance was added
C: absorbance in a well to which no test substance was added As a result, the compounds of the present invention inhibited the growth of breast cancer SK-BR-3 cells whereas none of comparative compounds inhibited the growth of SK-BR-3 cells (Table 20).

TABLE 20

| Example | HSP-binding activity IC50 (μm) | Cell growth inhibition IC50 (μM) |
|---|---|---|
| 1 | 0.17 | 0.02 |
| 3 | 0.74 | 0.56 |

TABLE 20-continued

| Example | HSP-binding activity IC50 (μm) | Cell growth inhibition IC50 (μM) |
|---|---|---|
| 4 | 0.16 | 0.14 |
| 5 | 0.24 | 0.27 |
| 6 | 0.10 | 0.03 |
| 7 | 0.37 | 1.19 |
| 8 | 0.11 | 0.11 |
| 9 | 0.26 | 0.01 |
| 10 | 0.25 | 0.10 |
| 11 | 0.30 | 0.08 |
| 12 | 0.12 | 0.06 |
| 13 | 0.20 | 0.06 |
| 14 | 0.27 | 0.01 |
| 15 | 0.23 | 0.02 |
| 16 | 0.29 | 0.03 |
| 17 | 0.49 | 0.30 |
| 18 | 0.09 | 0.05 |
| 19 | 0.17 | 0.10 |
| 20 | 0.14 | 0.09 |
| 21 | 0.15 | 0.07 |
| 22 | 0.14 | 0.12 |
| 23 | 0.28 | 0.17 |
| 24 | 0.08 | 0.13 |
| 25 | 0.10 | 0.17 |
| 46 | 0.19 | 0.05 |
| 47 | 0.43 | 0.12 |
| 48 | 0.26 | 0.01 |
| 49 | 0.12 | 0.03 |
| 50 | 0.25 | 0.01 |
| 51 | 0.16 | 0.06 |
| 52 | 0.42 | 0.02 |
| Comparative Example 1 | >100 | >10 |
| Comparative Example 2 | >100 | >10 |
| Comparative Example 3 | >10 | >10 |
| Comparative Example 4 | >10 | >10 |
| Comparative Example 5 | >100 | >10 |
| Comparative Example 6 | >100 | >10 |

Comparative tests of the compounds of the present invention were performed by testing the binding to HSP90 and testing the effect for inhibition of growth of SK-BR-3 cancer cell line, using the compounds described in Examples of Patent Document 2 as comparative compounds. The comparative compounds hardly exhibited inhibition activities in both tests even at high concentrations. Note that the comparative compounds were synthesized in accordance with the method described in Patent Document 2 (Table 21).

TABLE 21

| Compound | Structure |
|---|---|
| Comparative Example 1 | 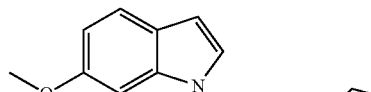 |

TABLE 21-continued

| Compound | Structure |
|---|---|
| Comparative Example 2 | 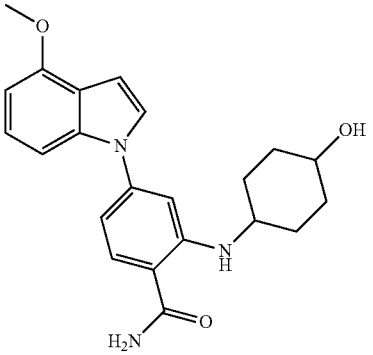 [SMILES: COc1cccc2c1ccn2-c1ccc(C(N)=O)c(NC2CCC(O)CC2)c1] |
| Comparative Example 3 | 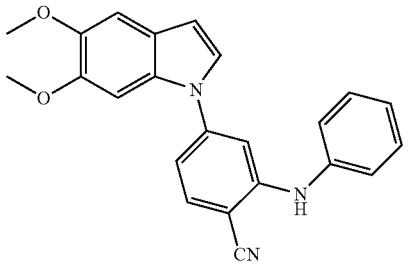 [SMILES: COc1cc2ccn(-c3ccc(C#N)c(Nc4ccccc4)c3)c2cc1OC] |
| Comparative Example 4 | 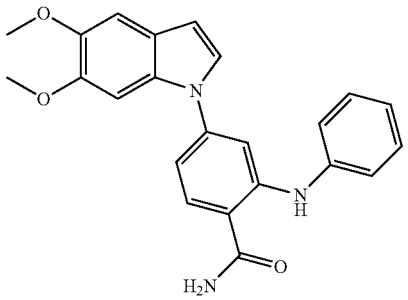 [SMILES: COc1cc2ccn(-c3ccc(C(N)=O)c(Nc4ccccc4)c3)c2cc1OC] |
| Comparative Example 5 | 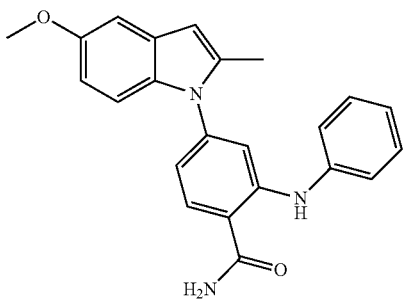 [SMILES: COc1ccc2c(c1)cc(C)n2-c1ccc(C(N)=O)c(Nc2ccccc2)c1] |
| Comparative Example 6 | 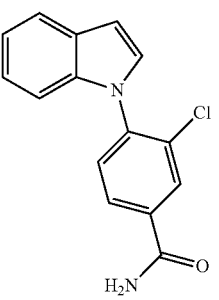 [SMILES: NC(=O)c1ccc(-n2ccc3ccccc32)c(Cl)c1] |

Test Example 3

Measurement of hERG-binding Activity

The hERG-binding activity was measured according to the package insert using Predictor hERG Fluorescence Polarization Assay Kit (PV5365, Invitrogen). A suspension of a lipid membrane expressing the hERG channel and a fluorescent labeled hERG-binding substance were added to a 384-well plate (No. 3677, manufactured by Corning Incorporated) containing test substances. After reaction at room temperature for 4 hours, fluorescence polarization was measured by a multi-label plate reader, EnVision (Perkin Elmer Inc.). The inhibition rate (%) of the binding of the fluorescent labeled hERG-binding substance by a compound of the present invention was determined by the following equation using the fluorescence polarization signal of a test substance-free group (control) as a control. Each compound was added thereto, and the concentration ($IC_{50}$ (μM)) of a compound to inhibit the binding of the fluorescent labeled hERG-binding substance to 50% of that of the control was determined as a relative index of hERG-binding activity.

Inhibition rate (%)=$(C-T)/C\times 100$

T: signal in a well to which a test substance was added
C: signal in a well to which no test substance was added As a result, since the compounds of the present invention showed the $IC_{50}$ values exceeding 30 μM and did not exhibit hERG inhibitory activity, they were considered to have a low risk of generating cardiotoxic side effects and to be highly safe.

Test Example 4

Evaluation of Antitumor Effect Using Subcutaneous Transplantation Models of Human Gastric Cancer Cell Lines (NCI-N87) (In Vivo)

Human gastric cancer cells (NCI-N87) (obtained from ATCC) were subcutaneously transplanted in nude mice, and at the time when the tumor volume of the nude mice in which the cancer cells had been survived became approximately 140 to 210 mm³, stratified randomization was performed so that the average tumor volume of each group (6 animals were assigned to one group (grouping: on day 0)) became uniform. The compounds 1, 6, and 9 of the present invention and the comparative compounds 6 (the compound of Example 21 in WO 2010/106290) and 7 (the compound of Example 1 in WO 2010/106290) were orally administered daily once per day from day 1 for 14 days. Note that the comparative compounds were synthesized according to the method described in WO 2010/106290 (Table 22).

TABLE 22

| Compound | Structure |
|---|---|
| Comparative Example 6 | 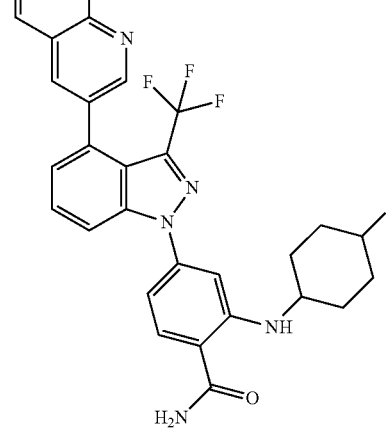 |
| Comparative Example 7 | 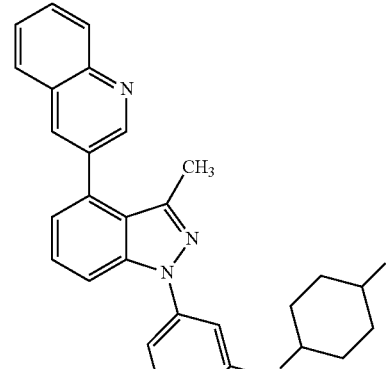 |

The doses of 2 mg/kg/day and 10 mg/kg/day were used for the comparative compounds 6 and 7, and the dose of 2 mg/kg/day was used for the compounds of Examples of 1, 6, and 9 of the present invention.

In order to compare the transition over time of the tumor growth in the administration of each test compound, the relative tumor volume (RTV) was calculated according to the following equation when the tumor volume on the grouping day was defined as 1 for the growth rate of tumor, and the transition of the average value of the RTV of each individual was shown in FIG. 1.

RTV=(Tumor volume on tumor volume measurement day)/(Tumor volume when grouped)  (Mathematical Formula 1)

In addition, the body weight of each individual was measured, and the body weight change (BWC) (%) from the weight on the grouping day was calculated according to the following equation. The transition of the average value of BWC in each individual was shown in FIG. 2.

BWC=(Body weight on tumor volume measurement day)/(Body weight when grouped)×10(Mathematical Formula 2)

When an average RTV value on the last evaluation day (on day 15 after the start of administration) of the group receiving the compound of Example of the present invention was smaller than that of the administration group of comparative compounds 6 and 7 and showed a statistical significant difference (Student-t test) for both of comparative compounds 6 and 7, the compounds of the Examples of the present invention were determined to be more significantly effective than the comparative compounds. Such effective cases were indicated in FIG. 1 by asterisk (*).

Figure 2:
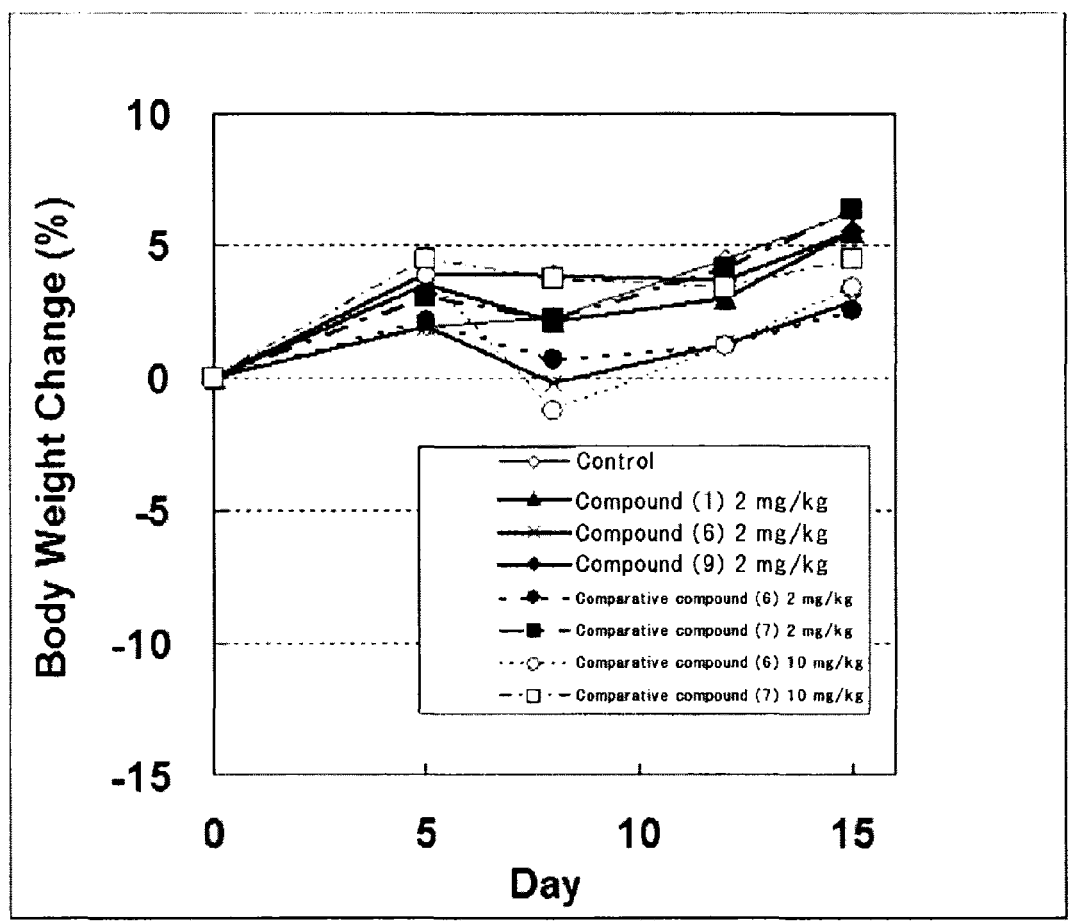
FIG. 2 is a graph showing weight change in mice to which the compound of the present invention is administered.

As shown in FIG. 1, when the compounds 1, 6, and 9 of the present invention were compared at a dose of 2 mg/kg/day respectively, it was revealed that all of them inhibited the tumor growth within one week from the start of the administration and showed significantly stronger anti-tumor effects than the comparative compounds 6 and 7 on day 15 from the start of the administration. In addition, even when only the dose of each of the comparative compounds 6 and 7 was increased to 10 mg/kg/day, it was revealed that all of the compounds in Examples 1, 6, and 9 of the present invention showed a significantly stronger anti-tumor effect than any of the comparative compounds 6 and 7. In this case, as shown in FIG. 2, the weight loss in nude mice treated with the compounds of the Example in the present invention was not observed in most tests and this also confirmed that the test was carried out at doses that did not develop the weight loss toxicity.

As described above, the compounds of the present invention caused a significantly stronger inhibition against tumor growth than the compounds having one unsaturated heterocyclic group at the $4^{th}$ position of the indazole ring and showed an excellent anti-tumor effect.

The invention claimed is:
1. A compound of formula:

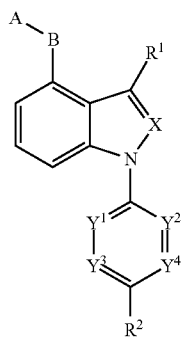

or a salt thereof,
wherein X represents CH or N;
any one or two of $Y^1, Y^2, Y^3$, and $Y^4$ represent C—$R^3$ or N, and others represent CH;
A and B independently represent a monocyclic 5- to 6-membered unsaturated heterocyclic group having 1 to 3 heteroatoms selected from the group consisting of N, S, and O, optionally substituted with at least one group selected from the group consisting of a halogen atom, a hydroxyl group, a cyano group, an amino group, a nitro group, an oxo group, a carboxyl group, a carbamoyl group, an alkyl group, a cycloalkyl group, an alkenyl group, an alkynyl group, an alkoxy group, an acyl group, an acyloxy group, an alkoxycarbonyl group, a saturated heterocyclic group, an unsaturated heterocyclic group, an aromatic hydrocarbon group, a halogenoalkyl group, an aralkyl group, an alkylamino group, an acylamino group, and an aralkyloxy group;
$R^1$ represents a hydrogen atom, an alkyl group having 1 to 6 carbon atoms, an cycloalkyl group having 3 to 7 carbon atoms, or an alkenyl group having 2 to 6 carbon atoms, wherein the alkyl group having 1 to 6 carbon atoms, the cycloalkyl group having 3 to 7 carbon atoms, or the alkenyl group having 2 to 6 carbon atoms is optionally substituted with at least one group selected from the group consisting of a halogen atom, a hydroxyl group, a cyano group, an amino group, a nitro group, an oxo group, a carboxyl group, a carbamoyl group, an alkyl group, a cycloalkyl group, an alkenyl group, an alkynyl group, an alkoxy group, an acyl group, an acyloxy group, an alkoxycarbonyl group, a saturated heterocyclic group, an unsaturated heterocyclic group, an aromatic hydrocarbon group, a halogenoalkyl group, an aralkyl group, an alkylamino group, an acylamino group, and an aralkyloxy group;

$R^2$ represents —CO—$R^4$;

$R^3$ represents a hydrogen atom, a halogen atom, an alkyl group having 1 to 6 carbon atoms, an alkoxy group having 1 to 6 carbon atoms, —CO—$R^5$, —N($R^6$)($R^7$), or —S—$R^8$;

$R^4$ and $R^5$ independently represent a hydroxyl group, an amino group, or an alkylamino group having 1 to 6 carbon atoms;

$R^6$ and $R^7$ independently represent a hydrogen atom, an alkyl group having 1 to 6 carbon atoms, or a cycloalkyl group having 3 to 7 carbon atoms; and $R^8$ represents a cycloalkyl group having 3 to 7 carbon atoms or an aromatic hydrocarbon group, each of which is optionally substituted with at least one group selected from the group consisting of a halogen atom, a hydroxyl group, a cyano group, an amino group, a nitro group, an oxo group, a carboxyl group, a carbamoyl group, an alkyl group, a cycloalkyl group, an alkenyl group, an alkynyl group, an alkoxy group, an acyl group, an acyloxy group, an alkoxycarbonyl group, a saturated heterocyclic group, an unsaturated heterocyclic group, an aromatic hydrocarbon group, a halogenoalkyl group, an aralkyl group, an alkylamino group, an acylamino group, and an aralkyloxy group.

2. The compound or a salt thereof according to claim 1, wherein $R^1$ is a hydrogen atom, an alkyl group having 1 to 6 carbon atoms, or a halogenoalkyl group having 1 to 6 carbon atoms.

3. The compound or a salt thereof according to claim 1, wherein $R^4$ is an amino group.

4. The compound or a salt thereof according to claim 1, wherein $R^3$ is a halogen atom, an alkyl group having 1 to 6 carbon atoms, or —N($R^6$)($R^7$) in which $R^6$ is a hydrogen atom and $R^7$ is a hydrogen atom, an alkyl group having 1 to 6 carbon atoms, or a cycloalkyl group having 3 to 7 carbon atoms.

5. The compound or a salt thereof according to claim 1, wherein $Y^4$ is C—$R^3$ or N and $Y^1$ to $Y^3$ are CH, or $Y^2$ to $Y^4$ are CH and $Y^1$ is C—$R^3$.

6. The compound or a salt thereof according to claim 1, wherein A is a monocyclic 5- to 6-membered unsaturated heterocyclic group having 1 to 3 heteroatoms selected from the group consisting of N, S, and O and optionally having an alkyl group having 1 to 6 carbon atoms, and B is a monocyclic 5- to 6-membered unsaturated heterocyclic group having 1 to 3 heteroatoms selected from the group consisting of N, S, and O.

7. A pharmaceutical composition, comprising:
the compound or a salt thereof according to claim 1 and a pharmaceutically acceptable carrier.

\* \* \* \* \*